(12) United States Patent
Kuroiwa et al.

(10) Patent No.: US 9,315,824 B2
(45) Date of Patent: Apr. 19, 2016

(54) HUMAN ARTIFICIAL CHROMOSOME VECTOR

(75) Inventors: Yoshimi Kuroiwa, Sioux Falls, SD (US); Hiroaki Matsushita, Sioux Falls, SD (US); Akiko Sano, Tokyo (JP)

(73) Assignee: SAB, LLC, Sioux Falls, SD (US)

( * ) Notice: Subject to any disclaimer, the term of this patent is extended or adjusted under 35 U.S.C. 154(b) by 144 days.

(21) Appl. No.: 13/510,327

(22) PCT Filed: Nov. 17, 2010

(86) PCT No.: PCT/JP2010/070514
§ 371 (c)(1),
(2), (4) Date: May 17, 2012

(87) PCT Pub. No.: WO2011/062207
PCT Pub. Date: May 26, 2011

(65) Prior Publication Data
US 2012/0222140 A1     Aug. 30, 2012

Related U.S. Application Data

(60) Provisional application No. 61/261,935, filed on Nov. 17, 2009.

(51) Int. Cl.
| | | |
|---|---|---|
| C12N 15/00 | (2006.01) | |
| C07H 21/02 | (2006.01) | |
| C12P 21/00 | (2006.01) | |
| A01K 67/027 | (2006.01) | |
| C12N 15/85 | (2006.01) | |
| C07K 16/00 | (2006.01) | |
| C07K 16/12 | (2006.01) | |

(52) U.S. Cl.
CPC ............... *C12N 15/85* (2013.01); *C07K 16/00* (2013.01); *C07K 16/1278* (2013.01); *C12N 15/8509* (2013.01); *A01K 2207/15* (2013.01); *A01K 2217/072* (2013.01); *A01K 2227/101* (2013.01); *A01K 2267/01* (2013.01); *C12N 2800/208* (2013.01)

(58) Field of Classification Search
None
See application file for complete search history.

(56) References Cited

U.S. PATENT DOCUMENTS

| | | | |
|---|---|---|---|
| 5,545,807 A * | 8/1996 | Surani et al. ........................ 800/6 |
| 5,625,126 A * | 4/1997 | Lonberg et al. .................. 800/18 |
| 5,874,299 A * | 2/1999 | Lonberg et al. ............. 435/320.1 |
| 7,371,568 B1 | 5/2008 | Tomizuka et al. |
| 7,476,536 B2 | 1/2009 | Kuroiwa et al. |
| 2004/0073957 A1 | 4/2004 | Tomizuka et al. |
| 2005/0002929 A1* | 1/2005 | Sanchez-Madrid et al. ............. 424/144.1 |
| 2006/0041945 A1* | 2/2006 | Robl et al. ........................ 800/6 |
| 2008/0026457 A1* | 1/2008 | Wells et al. ................. 435/320.1 |
| 2010/0004139 A1* | 1/2010 | Ramesh et al. .................. 506/14 |
| 2010/0047171 A1* | 2/2010 | Beckmann ...................... 424/9.1 |

FOREIGN PATENT DOCUMENTS

| | | |
|---|---|---|
| EP | 0972445 A1 | 1/2000 |
| WO | 9707671 A1 | 3/1997 |
| WO | 9837757 A1 | 9/1998 |
| WO | 0010383 A1 | 3/2000 |
| WO | 02070648 A2 | 9/2002 |
| WO | 02092812 A1 | 11/2002 |
| WO | 03097812 A2 | 11/2003 |
| WO | 2005104835 A2 | 11/2005 |
| WO | 2008118970 A2 | 10/2008 |
| WO | 2009111086 A1 | 9/2009 |

OTHER PUBLICATIONS

Mayforth, Ruth D. Ed. Designing Antibodies. Academic Press, San Diego. 1993. pp. 34-37.*
Mousavi et al. Characterization of the gene for the membrane and secretory form of the IgM heavy-chain constant region gene (Cmu) of the cow (Bos Taurus). Immunology, 1998. 93:581-588.*
International Search Report dated Feb. 1, 2011 issued in International Application No. PCT/JP2010/070514 (PCT/ISA/210).
Written Opinion dated Feb. 1, 2011 issued in International Application No. PCT/JP2010/070514 (PCT/ISA/237).
Tomizuka, et al. "Functional expression and germline transmission of a human chromosome fragment in chimaeric mice", Nature Genetics, vol. 16, Jun. 1997, pp. 133-143.
Kuroiwa, et al. "Manipulation of human minichromosomes to carry greater than megabase-sized chromosome inserts", Nature Biotechnology, vol. 18, Oct. 2000, pp. 1086-1090.
Dunham, et al. "The DNA sequence of human chromosome 22", Nature, vol. 402, Dec. 1999, pp. 489-496.
Kuroiwa, et al. "Cloned transchromosomic calves producing human immunoglobulin", Nature Biotechnology, vol. 20, Sep. 2002, pp. 889-894.
Kuroiwa, et al. "Sequential targeting of the genes encoding immunoglobulin-u and prion protein in cattle", Nature Genetics, vol. 36, No. 7, Jul. 2004, pp. 775-780.
Kuroiwa, et al. "Antigen-specific human polyclonal antibodies from hyperimmunized cattle", Nature Biotechnology, vol. 27, No. 2, Feb. 2009, pp. 173-181.
Tomizuka, et al. "Double trans-chromosomic mice: Maintenance of two individual human chromosome fragments containing Ig heave and k loci and expression of fully human antibodies", Proc. Natl. Acad. Sci. USA, vol. 97, No. 2, Jan. 18, 200, pp. 722-727.
International Search Report dated Feb. 1, 2011 issued in International Application No. PCT/JP2010/070513 (PCT/ISA/210).
Written Opinion dated Feb. 1, 2011 issued in International Application No. PCT/JP2010/070513(PCT/ISA/237).

(Continued)

*Primary Examiner* — Christopher M Babic
*Assistant Examiner* — Kimberly A Aron
(74) *Attorney, Agent, or Firm* — McDonnell Boehnen Hulbert & Berghoff LLP

(57) ABSTRACT

The present invention provides a human artificial chromosome vector comprising a gene encoding the human antibody heavy chain, a gene encoding the human antibody light chain, and a gene encoding IgM heavy chain constant region derived from a nonhuman animal; and being capable of producing a human antibody with a higher efficiency when the vector is introduced into an animal. By immunizing the animal produced using a human artificial chromosome vector of the present invention with a desired antigen, a large quantity of human polyclonal antibodies can be supplied.

22 Claims, 20 Drawing Sheets

(56) References Cited

OTHER PUBLICATIONS

Bankovich et al., "Structural Insight into Pre-B Cell Receptor Function" Science 316(5822):291-94 (2007).

Lonberg, "Human antibodies from transgenic animals" Nature Biotechnology 23(9):1117-25 (2005).

Penichet et al., "Design and engineering human forms of monoclonal antibodies" Drug Development Research 61(3):121-36 (2004).

Sano et al., "Physiological level production of antigen-specific human immunoglobulin in cloned transchromosomic cattle." PLoS One. 8(10):e78119 (Oct. 2013).

* cited by examiner pTEL'hisDpuro^lox2272F9R9

SEQUENCE LISTING

<160> NUMBER OF SEQ ID NOS: 96

<210> SEQ ID NO 1
<211> LENGTH: 41
<212> TYPE: DNA
<213> ORGANISM: Artificial
<220> FEATURE:
<223> OTHER INFORMATION: Artificially synthesized oligonucleotide

<400> SEQUENCE: 1
tcgaggatcc gccagggaga cagatgccaa gtacggttta g                          41

<210> SEQ ID NO 2
<211> LENGTH: 41
<212> TYPE: DNA
<213> ORGANISM: Artificial
<220> FEATURE:
<223> OTHER INFORMATION: Artificially synthesized oligonucleotide

<400> SEQUENCE: 2
tcgaggatcc aggatctttg ggggactgaa tggggtgtgc t                          41

<210> SEQ ID NO 3
<211> LENGTH: 46
<212> TYPE: DNA
<213> ORGANISM: Artificial
<220> FEATURE:
<223> OTHER INFORMATION: Artificially synthesized oligonucleotide

<400> SEQUENCE: 3
agcttggatc cataacttcg tataggatac tttatacgaa gttata                     46

<210> SEQ ID NO 4
<211> LENGTH: 46
<212> TYPE: DNA
<213> ORGANISM: Artificial
<220> FEATURE:
<223> OTHER INFORMATION: Artificially synthesized oligonucleotide

<400> SEQUENCE: 4
agcttataac ttcgtataaa gtatcctata cgaagttatg gatcca                     46

<210> SEQ ID NO 5
<211> LENGTH: 44
<212> TYPE: DNA
<213> ORGANISM: Artificial
<220> FEATURE:
<223> OTHER INFORMATION: Artificially synthesized oligonucleotide

<400> SEQUENCE: 5
tcgaggatcc ggcctcccaa aggattatag acgtgagcca ctgt                       44

<210> SEQ ID NO 6
<211> LENGTH: 45
<212> TYPE: DNA
<213> ORGANISM: Artificial
<220> FEATURE:
<223> OTHER INFORMATION: Artificially synthesized oligonucleotide

<400> SEQUENCE: 6
tcgaggatcc aaagaagggg cccgcctctg cctctaaatc ctgac                      45

<210> SEQ ID NO 7
<211> LENGTH: 29
<212> TYPE: DNA
<213> ORGANISM: Artificial

```
<220> FEATURE:
<223> OTHER INFORMATION: Artificially synthesized oligonucleotide

<400> SEQUENCE: 7
tgtagctgac tttagccacc cacaagtac                                              29

<210> SEQ ID NO 8
<211> LENGTH: 30
<212> TYPE: DNA
<213> ORGANISM: Artificial
<220> FEATURE:
<223> OTHER INFORMATION: Artificially synthesized oligonucleotide

<400> SEQUENCE: 8
cttgctgatt atacctcatc tccttccctc                                             30

<210> SEQ ID NO 9
<211> LENGTH: 46
<212> TYPE: DNA
<213> ORGANISM: Artificial
<220> FEATURE:
<223> OTHER INFORMATION: Artificially synthesized oligonucleotide

<400> SEQUENCE: 9
gtacaataac ttcgtatagc atacattata cgaagttata gatctg                           46

<210> SEQ ID NO 10
<211> LENGTH: 46
<212> TYPE: DNA
<213> ORGANISM: Artificial
<220> FEATURE:
<223> OTHER INFORMATION: Artificially synthesized oligonucleotide

<400> SEQUENCE: 10
aattcagatc tataacttcg tataatgtat gctatacgaa gttatt                           46

<210> SEQ ID NO 11
<211> LENGTH: 40
<212> TYPE: DNA
<213> ORGANISM: Artificial
<220> FEATURE:
<223> OTHER INFORMATION: Artificially synthesized oligonucleotide

<400> SEQUENCE: 11
gatctataac ttcgtatagg atactttata cgaagttatg                                  40

<210> SEQ ID NO 12
<211> LENGTH: 40
<212> TYPE: DNA
<213> ORGANISM: Artificial
<220> FEATURE:
<223> OTHER INFORMATION: Artificially synthesized oligonucleotide

<400> SEQUENCE: 12
ctagcataac ttcgtataaa gtatcctata cgaagttata                                  40

<210> SEQ ID NO 13
<211> LENGTH: 35
<212> TYPE: DNA
<213> ORGANISM: Artificial
<220> FEATURE:
<223> OTHER INFORMATION: Artificially synthesized oligonucleotide

<400> SEQUENCE: 13
gtacaatctt ggatcactac aacctctgcc tacca                                       35
```

<210> SEQ ID NO 14
<211> LENGTH: 35
<212> TYPE: DNA
<213> ORGANISM: Artificial
<220> FEATURE:
<223> OTHER INFORMATION: Artificially synthesized oligonucleotide

<400> SEQUENCE: 14
tgctgtgtct aatcaggtgt tgaacccatc tacta                           35

<210> SEQ ID NO 15
<211> LENGTH: 40
<212> TYPE: DNA
<213> ORGANISM: Artificial
<220> FEATURE:
<223> OTHER INFORMATION: Artificially synthesized oligonucleotide

<400> SEQUENCE: 15
gatctataac ttcgtatagt atacattata cgaagttatg                      40

<210> SEQ ID NO 16
<211> LENGTH: 40
<212> TYPE: DNA
<213> ORGANISM: Artificial
<220> FEATURE:
<223> OTHER INFORMATION: Artificially synthesized oligonucleotide

<400> SEQUENCE: 16
ctagcataac ttcgtataat gtatactata cgaagttata                      40

<210> SEQ ID NO 17
<211> LENGTH: 40
<212> TYPE: DNA
<213> ORGANISM: Artificial
<220> FEATURE:
<223> OTHER INFORMATION: Artificially synthesized oligonucleotide

<400> SEQUENCE: 17
tcgaggatcc ttcgccaccc caaagatgat tacagattac                      40

<210> SEQ ID NO 18
<211> LENGTH: 43
<212> TYPE: DNA
<213> ORGANISM: Artificial
<220> FEATURE:
<223> OTHER INFORMATION: Artificially synthesized oligonucleotide

<400> SEQUENCE: 18
tcgaggatcc tacactagaa gcacaaaccc caccattaca cat                  43

<210> SEQ ID NO 19
<211> LENGTH: 46
<212> TYPE: DNA
<213> ORGANISM: Artificial
<220> FEATURE:
<223> OTHER INFORMATION: Artificially synthesized oligonucleotide

<400> SEQUENCE: 19
agcttggatc cataacttcg tatagtatac attatacgaa gttata               46

<210> SEQ ID NO 20
<211> LENGTH: 46
<212> TYPE: DNA
<213> ORGANISM: Artificial
<220> FEATURE:
<223> OTHER INFORMATION: Artificially synthesized oligonucleotide

<400> SEQUENCE: 20
agcttataac ttcgtataat gtatactata cgaagttatg gatcca                   46

<210> SEQ ID NO 21
<211> LENGTH: 25
<212> TYPE: DNA
<213> ORGANISM: Artificial
<220> FEATURE:
<223> OTHER INFORMATION: Artificially synthesized oligonucleotide

<400> SEQUENCE: 21
cagtccccgg cagattcagg tgtcc                                          25

<210> SEQ ID NO 22
<211> LENGTH: 25
<212> TYPE: DNA
<213> ORGANISM: Artificial
<220> FEATURE:
<223> OTHER INFORMATION: Artificially synthesized oligonucleotide

<400> SEQUENCE: 22
gaaagtggca ttggggtggc tctcg                                          25

<210> SEQ ID NO 23
<211> LENGTH: 58
<212> TYPE: DNA
<213> ORGANISM: Artificial
<220> FEATURE:
<223> OTHER INFORMATION: Artificially synthesized oligonucleotide

<400> SEQUENCE: 23
ggaccaggtg gagactgtgc agtcctcacc cataactttc agggcctaca gcatgctg      58

<210> SEQ ID NO 24
<211> LENGTH: 58
<212> TYPE: DNA
<213> ORGANISM: Artificial
<220> FEATURE:
<223> OTHER INFORMATION: Artificially synthesized oligonucleotide

<400> SEQUENCE: 24
cagcatgctg taggccctga agttatggg tgaggactgc acagtctcca cctggtcc       58

<210> SEQ ID NO 25
<211> LENGTH: 25
<212> TYPE: DNA
<213> ORGANISM: Artificial
<220> FEATURE:
<223> OTHER INFORMATION: Artificially synthesized oligonucleotide

<400> SEQUENCE: 25
tatcaagggg gtgtcggaaa tcgtg                                          25

<210> SEQ ID NO 26
<211> LENGTH: 25
<212> TYPE: DNA
<213> ORGANISM: Artificial
<220> FEATURE:
<223> OTHER INFORMATION: Artificially synthesized oligonucleotide

<400> SEQUENCE: 26
actgggcctg ggagaacctg agact                                          25

<210> SEQ ID NO 27

```
<211> LENGTH: 24
<212> TYPE: DNA
<213> ORGANISM: Artificial
<220> FEATURE:
<223> OTHER INFORMATION: Artificially synthesized oligonucleotide

<400> SEQUENCE: 27
gaggtgggct gagggggcaag tgtg                                          24

<210> SEQ ID NO 28
<211> LENGTH: 25
<212> TYPE: DNA
<213> ORGANISM: Artificial
<220> FEATURE:
<223> OTHER INFORMATION: Artificially synthesized oligonucleotide

<400> SEQUENCE: 28
tacgaggagg ggaggcagtg agagg                                          25

<210> SEQ ID NO 29
<211> LENGTH: 35
<212> TYPE: DNA
<213> ORGANISM: Artificial
<220> FEATURE:
<223> OTHER INFORMATION: Artificially synthesized oligonucleotide

<400> SEQUENCE: 29
gtcagccagg cgggccattt accgtaagtt atgta                               35

<210> SEQ ID NO 30
<211> LENGTH: 35
<212> TYPE: DNA
<213> ORGANISM: Artificial
<220> FEATURE:
<223> OTHER INFORMATION: Artificially synthesized oligonucleotide

<400> SEQUENCE: 30
agggctgggt tagatggcac caaatgaaag gagaa                               35

<210> SEQ ID NO 31
<211> LENGTH: 20
<212> TYPE: DNA
<213> ORGANISM: Artificial
<220> FEATURE:
<223> OTHER INFORMATION: Artificially synthesized oligonucleotide

<400> SEQUENCE: 31
tggaaggtgg ataacgccct                                                20

<210> SEQ ID NO 32
<211> LENGTH: 22
<212> TYPE: DNA
<213> ORGANISM: Artificial
<220> FEATURE:
<223> OTHER INFORMATION: Artificially synthesized oligonucleotide

<400> SEQUENCE: 32
tcattctcct ccaacattag ca                                             22

<210> SEQ ID NO 33
<211> LENGTH: 20
<212> TYPE: DNA
<213> ORGANISM: Artificial
<220> FEATURE:
<223> OTHER INFORMATION: Artificially synthesized oligonucleotide

<400> SEQUENCE: 33
```
agtcagggca ttagcagtgc                                          20

<210> SEQ ID NO 34
<211> LENGTH: 20
<212> TYPE: DNA
<213> ORGANISM: Artificial
<220> FEATURE:
<223> OTHER INFORMATION: Artificially synthesized oligonucleotide

<400> SEQUENCE: 34
gctgctgatg gtgagagtga                                          20

<210> SEQ ID NO 35
<211> LENGTH: 24
<212> TYPE: DNA
<213> ORGANISM: Artificial
<220> FEATURE:
<223> OTHER INFORMATION: Artificially synthesized oligonucleotide

<400> SEQUENCE: 35
cttacccagg ctccaggctc tatt                                     24

<210> SEQ ID NO 36
<211> LENGTH: 25
<212> TYPE: DNA
<213> ORGANISM: Artificial
<220> FEATURE:
<223> OTHER INFORMATION: Artificially synthesized oligonucleotide

<400> SEQUENCE: 36
ctctacctcc ctaccccatc atcac                                    25

<210> SEQ ID NO 37
<211> LENGTH: 22
<212> TYPE: DNA
<213> ORGANISM: Artificial
<220> FEATURE:
<223> OTHER INFORMATION: Artificially synthesized oligonucleotide

<400> SEQUENCE: 37
aggtgctgct gggtggtcaa gt                                       22

<210> SEQ ID NO 38
<211> LENGTH: 23
<212> TYPE: DNA
<213> ORGANISM: Artificial
<220> FEATURE:
<223> OTHER INFORMATION: Artificially synthesized oligonucleotide

<400> SEQUENCE: 38
gctcctgcaa atgtctcctg tca                                      23

<210> SEQ ID NO 39
<211> LENGTH: 26
<212> TYPE: DNA
<213> ORGANISM: Artificial
<220> FEATURE:
<223> OTHER INFORMATION: Artificially synthesized oligonucleotide

<400> SEQUENCE: 39
tctttctctc acctaattgt cctggc                                   26

<210> SEQ ID NO 40
<211> LENGTH: 24
<212> TYPE: DNA

```
<213> ORGANISM: Artificial
<220> FEATURE:
<223> OTHER INFORMATION: Artificially synthesized oligonucleotide

<400> SEQUENCE: 40
aggactggca ctcttgtcga tacc                                          24

<210> SEQ ID NO 41
<211> LENGTH: 25
<212> TYPE: DNA
<213> ORGANISM: Artificial
<220> FEATURE:
<223> OTHER INFORMATION: Artificially synthesized oligonucleotide

<400> SEQUENCE: 41
agatctcttg agcccagcag tttga                                         25

<210> SEQ ID NO 42
<211> LENGTH: 24
<212> TYPE: DNA
<213> ORGANISM: Artificial
<220> FEATURE:
<223> OTHER INFORMATION: Artificially synthesized oligonucleotide

<400> SEQUENCE: 42
tgaagttagc cggggataca gacg                                          24

<210> SEQ ID NO 43
<211> LENGTH: 25
<212> TYPE: DNA
<213> ORGANISM: Artificial
<220> FEATURE:
<223> OTHER INFORMATION: Artificially synthesized oligonucleotide

<400> SEQUENCE: 43
tgtcctgggc tcctgtcctg ctcat                                         25

<210> SEQ ID NO 44
<211> LENGTH: 20
<212> TYPE: DNA
<213> ORGANISM: Artificial
<220> FEATURE:
<223> OTHER INFORMATION: Artificially synthesized oligonucleotide

<400> SEQUENCE: 44
ggcggcggct ccaccctctt                                               20

<210> SEQ ID NO 45
<211> LENGTH: 22
<212> TYPE: DNA
<213> ORGANISM: Artificial
<220> FEATURE:
<223> OTHER INFORMATION: Artificially synthesized oligonucleotide

<400> SEQUENCE: 45
cactgcctgc ccgctgctgg ta                                            22

<210> SEQ ID NO 46
<211> LENGTH: 21
<212> TYPE: DNA
<213> ORGANISM: Artificial
<220> FEATURE:
<223> OTHER INFORMATION: Artificially synthesized oligonucleotide

<400> SEQUENCE: 46
gggcggggaa gtgggggaga g                                             21
```

<210> SEQ ID NO 47
<211> LENGTH: 22
<212> TYPE: DNA
<213> ORGANISM: Artificial
<220> FEATURE:
<223> OTHER INFORMATION: Artificially synthesized oligonucleotide

<400> SEQUENCE: 47
ggagaccacc aaaccctcca aa                                    22

<210> SEQ ID NO 48
<211> LENGTH: 22
<212> TYPE: DNA
<213> ORGANISM: Artificial
<220> FEATURE:
<223> OTHER INFORMATION: Artificially synthesized oligonucleotide

<400> SEQUENCE: 48
gagagttgca gaagggtga ct                                     22

<210> SEQ ID NO 49
<211> LENGTH: 20
<212> TYPE: DNA
<213> ORGANISM: Artificial
<220> FEATURE:
<223> OTHER INFORMATION: Artificially synthesized oligonucleotide

<400> SEQUENCE: 49
atcatctgct cgctctctcc                                       20

<210> SEQ ID NO 50
<211> LENGTH: 20
<212> TYPE: DNA
<213> ORGANISM: Artificial
<220> FEATURE:
<223> OTHER INFORMATION: Artificially synthesized oligonucleotide

<400> SEQUENCE: 50
cacatctgta gtggctgtgg                                       20

<210> SEQ ID NO 51
<211> LENGTH: 25
<212> TYPE: DNA
<213> ORGANISM: Artificial
<220> FEATURE:
<223> OTHER INFORMATION: Artificially synthesized oligonucleotide

<400> SEQUENCE: 51
agccccaaga acccagccga tgtga                                 25

<210> SEQ ID NO 52
<211> LENGTH: 25
<212> TYPE: DNA
<213> ORGANISM: Artificial
<220> FEATURE:
<223> OTHER INFORMATION: Artificially synthesized oligonucleotide

<400> SEQUENCE: 52
ggcagaggga gtgtggggtg ttgtg                                 25

<210> SEQ ID NO 53
<211> LENGTH: 20
<212> TYPE: DNA
<213> ORGANISM: Artificial
<220> FEATURE:

<223> OTHER INFORMATION: Artificially synthesized oligonucleotide

<400> SEQUENCE: 53
accagcgcgt catcatcaag                                              20

<210> SEQ ID NO 54
<211> LENGTH: 20
<212> TYPE: DNA
<213> ORGANISM: Artificial
<220> FEATURE:
<223> OTHER INFORMATION: Artificially synthesized oligonucleotide

<400> SEQUENCE: 54
atcgccagcc tcaccatttc                                              20

<210> SEQ ID NO 55
<211> LENGTH: 35
<212> TYPE: DNA
<213> ORGANISM: Artificial
<220> FEATURE:
<223> OTHER INFORMATION: Artificially synthesized oligonucleotide

<400> SEQUENCE: 55
gtcagccagg cgggccattt accgtaagtt atgta                             35

<210> SEQ ID NO 56
<211> LENGTH: 35
<212> TYPE: DNA
<213> ORGANISM: Artificial
<220> FEATURE:
<223> OTHER INFORMATION: Artificially synthesized oligonucleotide

<400> SEQUENCE: 56
agggctgggt tagatggcac caaatgaaag gagaa                             35

<210> SEQ ID NO 57
<211> LENGTH: 23
<212> TYPE: DNA
<213> ORGANISM: Artificial
<220> FEATURE:
<223> OTHER INFORMATION: Artificially synthesized oligonucleotide

<400> SEQUENCE: 57
gcggcgccgg caggaaggaa atg                                          23

<210> SEQ ID NO 58
<211> LENGTH: 22
<212> TYPE: DNA
<213> ORGANISM: Artificial
<220> FEATURE:
<223> OTHER INFORMATION: Artificially synthesized oligonucleotide

<400> SEQUENCE: 58
cgaggcgcac cgtgggcttg ta                                           22

<210> SEQ ID NO 59
<211> LENGTH: 27
<212> TYPE: DNA
<213> ORGANISM: Artificial
<220> FEATURE:
<223> OTHER INFORMATION: Artificially synthesized oligonucleotide

<400> SEQUENCE: 59
acggcgtgag gaccaaggag cgaaacc                                      27

```
<210> SEQ ID NO 60
<211> LENGTH: 28
<212> TYPE: DNA
<213> ORGANISM: Artificial
<220> FEATURE:
<223> OTHER INFORMATION: Artificially synthesized oligonucleotide

<400> SEQUENCE: 60
tgagcgacga attaaaacag gcgatgac                                      28

<210> SEQ ID NO 61
<211> LENGTH: 24
<212> TYPE: DNA
<213> ORGANISM: Artificial
<220> FEATURE:
<223> OTHER INFORMATION: Artificially synthesized oligonucleotide

<400> SEQUENCE: 61
gggcaacata gcaagacacc attc                                          24

<210> SEQ ID NO 62
<211> LENGTH: 25
<212> TYPE: DNA
<213> ORGANISM: Artificial
<220> FEATURE:
<223> OTHER INFORMATION: Artificially synthesized oligonucleotide

<400> SEQUENCE: 62
tcctctcacc tcagcctcca tagta                                         25

<210> SEQ ID NO 63
<211> LENGTH: 35
<212> TYPE: DNA
<213> ORGANISM: Artificial
<220> FEATURE:
<223> OTHER INFORMATION: Artificially synthesized oligonucleotide

<400> SEQUENCE: 63
actgaaatat tttaaatgtt tgcccttccc actcc                              35

<210> SEQ ID NO 64
<211> LENGTH: 32
<212> TYPE: DNA
<213> ORGANISM: Artificial
<220> FEATURE:
<223> OTHER INFORMATION: Artificially synthesized oligonucleotide

<400> SEQUENCE: 64
agacctccgc gccccgcaac ctccccttct ac                                 32

<210> SEQ ID NO 65
<211> LENGTH: 23
<212> TYPE: DNA
<213> ORGANISM: Artificial
<220> FEATURE:
<223> OTHER INFORMATION: Artificially synthesized oligonucleotide

<400> SEQUENCE: 65
aacagttgaa tttatgggga gtc                                           23

<210> SEQ ID NO 66
<211> LENGTH: 25
<212> TYPE: DNA
<213> ORGANISM: Artificial
<220> FEATURE:
<223> OTHER INFORMATION: Artificially synthesized oligonucleotide
```

<400> SEQUENCE: 66
tcaggcttta aacacagtat cacag                                              25

<210> SEQ ID NO 67
<211> LENGTH: 28
<212> TYPE: DNA
<213> ORGANISM: Artificial
<220> FEATURE:
<223> OTHER INFORMATION: Artificially synthesized oligonucleotide

<400> SEQUENCE: 67
acgcctgctc gcctgcccgc tcgcttct                                           28

<210> SEQ ID NO 68
<211> LENGTH: 27
<212> TYPE: DNA
<213> ORGANISM: Artificial
<220> FEATURE:
<223> OTHER INFORMATION: Artificially synthesized oligonucleotide

<400> SEQUENCE: 68
ttgccagggc cacagttaac ggatacg                                            27

<210> SEQ ID NO 69
<211> LENGTH: 25
<212> TYPE: DNA
<213> ORGANISM: Artificial
<220> FEATURE:
<223> OTHER INFORMATION: Artificially synthesized oligonucleotide

<400> SEQUENCE: 69
cagcacccca acggcaacaa agaaa                                              25

<210> SEQ ID NO 70
<211> LENGTH: 24
<212> TYPE: DNA
<213> ORGANISM: Artificial
<220> FEATURE:
<223> OTHER INFORMATION: Artificially synthesized oligonucleotide

<400> SEQUENCE: 70
ccccagggct gcactcacca acat                                               24

<210> SEQ ID NO 71
<211> LENGTH: 30
<212> TYPE: DNA
<213> ORGANISM: Artificial
<220> FEATURE:
<223> OTHER INFORMATION: Artificially synthesized oligonucleotide

<400> SEQUENCE: 71
tgcaggtgaa gtgacggcca gccaagaaca                                         30

<210> SEQ ID NO 72
<211> LENGTH: 33
<212> TYPE: DNA
<213> ORGANISM: Artificial
<220> FEATURE:
<223> OTHER INFORMATION: Artificially synthesized oligonucleotide

<400> SEQUENCE: 72
tggcagcagg gtgacaggga aggcagggaa aag                                     33

<210> SEQ ID NO 73
<211> LENGTH: 20

```
<212> TYPE: DNA
<213> ORGANISM: Artificial
<220> FEATURE:
<223> OTHER INFORMATION: Artificially synthesized oligonucleotide

<400> SEQUENCE: 73
agtgagataa gcagtggatg                                              20

<210> SEQ ID NO 74
<211> LENGTH: 20
<212> TYPE: DNA
<213> ORGANISM: Artificial
<220> FEATURE:
<223> OTHER INFORMATION: Artificially synthesized oligonucleotide

<400> SEQUENCE: 74
cttgtgctac tcccatcact                                              20

<210> SEQ ID NO 75
<211> LENGTH: 25
<212> TYPE: DNA
<213> ORGANISM: Artificial
<220> FEATURE:
<223> OTHER INFORMATION: Artificially synthesized oligonucleotide

<400> SEQUENCE: 75
accccaaagg ccaaactctc cactc                                        25

<210> SEQ ID NO 76
<211> LENGTH: 24
<212> TYPE: DNA
<213> ORGANISM: Artificial
<220> FEATURE:
<223> OTHER INFORMATION: Artificially synthesized oligonucleotide

<400> SEQUENCE: 76
cacttgtact ccttgccatt cagc                                         24

<210> SEQ ID NO 77
<211> LENGTH: 29
<212> TYPE: DNA
<213> ORGANISM: Artificial
<220> FEATURE:
<223> OTHER INFORMATION: Artificially synthesized oligonucleotide

<400> SEQUENCE: 77
gccctcacct tgcagaccac ctccatcat                                    29

<210> SEQ ID NO 78
<211> LENGTH: 30
<212> TYPE: DNA
<213> ORGANISM: Artificial
<220> FEATURE:
<223> OTHER INFORMATION: Artificially synthesized oligonucleotide

<400> SEQUENCE: 78
cctctcctgc tcagtcccct tccttccatc                                   30

<210> SEQ ID NO 79
<211> LENGTH: 22
<212> TYPE: DNA
<213> ORGANISM: Artificial
<220> FEATURE:
<223> OTHER INFORMATION: Artificially synthesized oligonucleotide

<400> SEQUENCE: 79
```
tgttctcctc ttcctcatct cc                                              22

<210> SEQ ID NO 80
<211> LENGTH: 22
<212> TYPE: DNA
<213> ORGANISM: Artificial
<220> FEATURE:
<223> OTHER INFORMATION: Artificially synthesized oligonucleotide

<400> SEQUENCE: 80
tgaaggtagt gaccagtgtt gg                                              22

<210> SEQ ID NO 81
<211> LENGTH: 30
<212> TYPE: DNA
<213> ORGANISM: Artificial
<220> FEATURE:
<223> OTHER INFORMATION: Artificially synthesized oligonucleotide

<400> SEQUENCE: 81
tgcaggtgaa gtgacggcca gccaagaaca                                      30

<210> SEQ ID NO 82
<211> LENGTH: 33
<212> TYPE: DNA
<213> ORGANISM: Artificial
<220> FEATURE:
<223> OTHER INFORMATION: Artificially synthesized oligonucleotide

<400> SEQUENCE: 82
tggcagcagg gtgacaggga aggcagggaa aag                                  33

<210> SEQ ID NO 83
<211> LENGTH: 25
<212> TYPE: DNA
<213> ORGANISM: Artificial
<220> FEATURE:
<223> OTHER INFORMATION: Artificially synthesized oligonucleotide

<400> SEQUENCE: 83
acgtcgccgg agcggtcgag ttctg                                           25

<210> SEQ ID NO 84
<211> LENGTH: 25
<212> TYPE: DNA
<213> ORGANISM: Artificial
<220> FEATURE:
<223> OTHER INFORMATION: Artificially synthesized oligonucleotide

<400> SEQUENCE: 84
tcggccacga agtgcacgca gttgc                                           25

<210> SEQ ID NO 85
<211> LENGTH: 20
<212> TYPE: DNA
<213> ORGANISM: Artificial
<220> FEATURE:
<223> OTHER INFORMATION: Artificially synthesized oligonucleotide

<400> SEQUENCE: 85
aaaacaggct ctagcgttcg                                                 20

<210> SEQ ID NO 86
<211> LENGTH: 20
<212> TYPE: DNA
<213> ORGANISM: Artificial

```
<220> FEATURE:
<223> OTHER INFORMATION: Artificially synthesized oligonucleotide

<400> SEQUENCE: 86
ttcggatcat cagctacacc                                                    20

<210> SEQ ID NO 87
<211> LENGTH: 23
<212> TYPE: DNA
<213> ORGANISM: Artificial
<220> FEATURE:
<223> OTHER INFORMATION: Artificially synthesized oligonucleotide

<400> SEQUENCE: 87
tggatgtatc ctgtcaagag acc                                                23

<210> SEQ ID NO 88
<211> LENGTH: 22
<212> TYPE: DNA
<213> ORGANISM: Artificial
<220> FEATURE:
<223> OTHER INFORMATION: Artificially synthesized oligonucleotide

<400> SEQUENCE: 88
cagacactct atgcctgtgt gg                                                 22

<210> SEQ ID NO 89
<211> LENGTH: 35
<212> TYPE: DNA
<213> ORGANISM: Artificial
<220> FEATURE:
<223> OTHER INFORMATION: Artificially synthesized oligonucleotide

<400> SEQUENCE: 89
actgaaatat tttaaatgtt tgcccttccc actcc                                   35

<210> SEQ ID NO 90
<211> LENGTH: 32
<212> TYPE: DNA
<213> ORGANISM: Artificial
<220> FEATURE:
<223> OTHER INFORMATION: Artificially synthesized oligonucleotide

<400> SEQUENCE: 90
agacctccgc gccccgcaac ctcccctct ac                                       32

<210> SEQ ID NO 91
<211> LENGTH: 25
<212> TYPE: DNA
<213> ORGANISM: Artificial
<220> FEATURE:
<223> OTHER INFORMATION: Artificially synthesized oligonucleotide

<400> SEQUENCE: 91
cagcacccca acggcaacaa agaaa                                              25

<210> SEQ ID NO 92
<211> LENGTH: 24
<212> TYPE: DNA
<213> ORGANISM: Artificial
<220> FEATURE:
<223> OTHER INFORMATION: Artificially synthesized oligonucleotide

<400> SEQUENCE: 92
ccccagggct gcactcacca acat                                               24
```

```
<210> SEQ ID NO 93
<211> LENGTH: 30
<212> TYPE: DNA
<213> ORGANISM: Artificial
<220> FEATURE:
<223> OTHER INFORMATION: Artificially synthesized oligonucleotide

<400> SEQUENCE: 93
tgcaggtgaa gtgacggcca gccaagaaca                                    30

<210> SEQ ID NO 94
<211> LENGTH: 33
<212> TYPE: DNA
<213> ORGANISM: Artificial
<220> FEATURE:
<223> OTHER INFORMATION: Artificially synthesized oligonucleotide

<400> SEQUENCE: 94
tggcagcagg gtgacaggga aggcagggaa aag                                33

<210> SEQ ID NO 95
<211> LENGTH: 20
<212> TYPE: DNA
<213> ORGANISM: Artificial
<220> FEATURE:
<223> OTHER INFORMATION: Artificially synthesized oligonucleotide

<400> SEQUENCE: 95
gccattgtcg agcaggtagt                                               20

<210> SEQ ID NO 96
<211> LENGTH: 20
<212> TYPE: DNA
<213> ORGANISM: Artificial
<220> FEATURE:
<223> OTHER INFORMATION: Artificially synthesized oligonucleotide

<400> SEQUENCE: 96
tccctcatca gccatcctaa                                               20
```

HUMAN ARTIFICIAL CHROMOSOME VECTOR

TECHNICAL FIELD

The present invention relates to a human artificial chromosome vector comprising a human antibody heavy chain gene, a human antibody light chain gene, and an IgM heavy chain constant region gene derived from a non-human animal, an animal having the human artificial chromosome vector, and a method for producing a human antibody.

BACKGROUND ART

The development of a technology of producing a chimeric animal by fusing micronuclei comprising human chromosome fragments with cells having pluripotent differentiation to obtain hybrid cells allows to prepare a non-human animal maintaining large exogenous genes to be produced (Non-Patent Document 1 and Patent Document 1).

Subsequently, a method for constructing a desired human artificial chromosome (hereinafter abbreviated to HAC) vector to produce the non-human animal has been proposed, by which the HAC including a wide range of human antibody gene loci has been established.

First, as a method for modifying a chromosome fragment to be introduced into a non-human animal, a technology of preparing a deleted chromosome with a high efficiency by inserting a telomere sequence into a desired sequence on a human chromosome kept in a chicken DT40 cell by gene targeting has been developed (Patent Document 2).

Further, in a process of maintaining a mouse cell keeping a human chromosome, it has been found that a fragment SC20 comprising an antibody heavy chain gene locus derived from the human chromosome 14 may be obtained, and the fragment is stably maintained in an embryonic stem (ES) cell and an individual of the mouse and has high transmission efficiency to progeny (Patent Document 2).

Therefore, a λHAC comprising a human antibody heavy chain and a human antibody λ chain was constructed by translocating a fragment comprising the antibody λ type light chain gene locus on the human chromosome 22 through the Cre/loxP site specific recombination system using such SC20 as a basic skeleton of a vector (Non-Patent Document 2 and Patent Document 3).

The λHAC has the stability and transmission efficiency to progeny almost equivalent to the SC20 and a chimeric mouse which stably maintains a λHAC is produced by introducing the λHAC into the mouse ES cells (Non-Patent Document 2 and Patent Document 3). It is now possible to construct a HAC vector including a human chromosome region having a specific megabase (Mb) size by the method.

Further, for the purpose of removing chromosome regions which adversely affect the generation of a chromosome-introduced animal, chromosome fragments ΔHAC and ΔΔHAC with an optimal size including the antibody λ type light chain (λ chain) gene region were prepared (Patent Document 4), based on the structural information of the human chromosome 22 (Non-Patent Document 3).

It was confirmed that the ΔHAC and ΔΔHAC include regions having 2.5 Mb and 1.5 Mb sizes, respectively, which are shorter than the periphery of the antibody λ type light chain gene region on the λHAC, 10 Mb, to impart a transmission efficiency to progeny higher than that of the λHAC (Patent Document 4).

Meanwhile, human polyclonal antibodies currently used for treatment and prevention of various diseases are prepared from a serum pool obtained from a plurality of human donors. For this reason, the performance of the human polyclonal antibodies depends largely on human donor sera as a supplying source, and thus a process of selecting a donor having a desired antigen reactivity or titer is required in preparing.

In addition, due to factors such as the kind of antigen, the number of exposure to an immunogen, and the amount of donor serum which may be collected, in preparing a polyclonal antibody, the development of the use thereof is limited. Therefore, a transgenic animal having a human antibody gene locus as a means for producing human polyclonal antibodies has been prepared.

Due to its body size, an ungulate animal is useful as a source of supplying a large quantity of human polyclonal antibodies. So far, in order to produce human polyclonal antibodies, a bovine into which the above-described HAC, specifically ΔHAC and ΔΔHAC are introduced to produce human polyclonal antibodies, is known (Non-Patent Document 4 and Patent Document 5).

In the neonatal sera of the bovine into which these HACs were introduced, 13 to 258 ng/mL of the human immunoglobulin (Ig) G was produced (Non-Patent Document 4).

Subsequently, in order to eliminate bovine antibodies produced in a bovine living body, gene targeting was carried out on IGHM and IGHML1 encoding the functional IgM genes among bovine endogenous antibody heavy chain genes and as a result, a bovine in which antibody heavy chains were knockout was known (Non-Patent Documents 5 and 6 and Patent Documents 6 and 7).

When ΔΔHAC was introduced into the obtained antibody heavy chain double-knockout bovine (IgHM$^{-/-}$/IgHML1$^{-/-}$ bovine), it was found 7.1 μg/mL of a human IgG was produced in a serum of a 14-day-old calf (Patent Document 7).

In addition, a bovine into which κHAC which is a HAC vector having a human antibody heavy chain gene locus and a human antibody κ type light chain (κ chain) gene locus was introduced was produced (Non-Patent Document 6 and Patent Document 8). κHAC is a vector constructed by translocating a fragment comprising the antibody κ chain gene locus on the human chromosome 2 onto the SC20. In FIG. 1, a schematic view of κHAC is shown.

Among IgHM$^{-/-}$/IgHML1$^{-/-}$ bovines into which κHAC was introduced, clone 468 which was the highest antibody producing individual constantly produced a human IgG at 1 g/L or more in the serum from the 84 days after birth, and exhibited a titer exceeding 2 g/L at the 210 days after birth.

However, a technology of stably producing an individual which exhibits high titer as described above has not been known, and thus there is a need for animals which produce human antibodies with higher efficiency or a technology which can stably produce these animals.

CITATION LIST

Patent Document

Patent Document 1: WO97/07671
Patent Document 2: WO98/37757
Patent Document 3: WO00/10383
Patent Document 4: WO02/92812
Patent Document 5: WO2002/70648
Patent Document 6: WO03/97812
Patent Document 7: WO05/104835
Patent Document 8: WO09/111,086

Non-Patent Document

Non-Patent Document 1: Tomizuka et al., *Nature Genetics*, 16, 133-143, 1997

Non-Patent Document 2: Kuroiwa et al., *Nature Biotechnology*, 18, 1086-1090, 2000

Non-Patent Document 3: Dunham et al., *Nature*, 402, 489-495, 1999

Non-Patent Document 4: Kuroiwa et al., *Nature Biotechnology*, 20, 889-894, 2002

Non-Patent Document 5: Kuroiwa et al., *Nature Genetics*, 36, 775-780, 2004

Non-Patent Document 6: Kuroiwa et al., *Nature Biotechnology*, 27, 173-181, 2009

SUMMARY OF INVENTION

Technical Problem

It is an object of the present invention to provide an animal for producing human antibodies efficiently, a method for stably supplying the animal, and a method for producing human antibodies with high efficiency.

Solution to Problems

Considering the above object, the present inventors modified the HAC vector for the purpose of achieving high production amount of the human IgG and stably producing a bovine individual with a high titer, compared to the conventional HAC.

That is, the present invention relates to the following (1) to (8).

(1) A human artificial chromosome vector comprising a gene encoding a human antibody heavy chain, a gene encoding a human antibody light chain, and a gene encoding an IgM heavy chain constant region derived from a non-human animal.

(2) The human artificial chromosome vector described in (1), comprising a gene encoding a human antibody surrogate light chain.

(3) The human artificial chromosome vector described in (2), in which a gene encoding a human antibody surrogate light chain is the VpreB gene and the λ5 gene.

(4) The human artificial chromosome vector described in any one of (1) to (3), in which the gene encoding the non-human animal-derived IgM heavy chain constant region is the bovine-derived IGHM.

(5) An animal having the human artificial chromosome vector described in any one of (1) to (3).

(6) A bovine having the human artificial chromosome vector described in (4).

(7) A method for producing a human antibody, comprising: administering a target antigen into an animal described in (5) to produce and accumulate the human antibody specific to the antigen in serum of the animal, and recovering the human antibody specific to the antigen from the serum.

(8) A method for producing a human antibody, comprising: administering a target antigen into a bovine described in (6) to produce and accumulate the human antibody specific to the antigen in serum of the bovine, and recovering the human antibody specific to the antigen from the serum.

Advantageous Effects of the Invention

Human antibodies may be produced with high efficiency by introducing the human artificial chromosome vector comprising a gene encoding the human antibody heavy chain, a gene encoding the human antibody light chain, and a gene encoding the IgM heavy chain constant region derived from a non-human animal of the present invention into an animal as compared to the vector produced by the conventional HAC technology. In addition, an animal which is capable of producing a human antibody with high efficiency may be stably produced by introducing the human artificial chromosome vector of the present invention into an animal.

Furthermore, as a preferred embodiment, when a human artificial chromosome vector which further comprises a human antibody surrogate light chain gene in addition to a gene encoding the human antibody heavy chain, a gene encoding the human antibody light chain, and a gene encoding the non-human animal-derived IgM heavy chain constant region, is introduced into an animal, a human antibody may be produced with a further higher efficiency, and an animal which is capable of producing a human antibody with such high efficiency may be stably produced.

BRIEF DESCRIPTION OF THE DRAWINGS

In FIG. 1(b), the dotted-line represents a human-derived IgM part, and the solid-line represents a bovine-derived IgM part.

In FIG. 2(b), the dotted-line represents a human-derived IgM part, and the solid-line represents a bovine-derived IgM part.

In FIG. 3(b), the dotted-line represents a human-derived IgM part, and the solid-line represents a bovine-derived IgM part.

EMBODIMENTS FOR CARRYING OUT THE INVENTION

Figure 1:
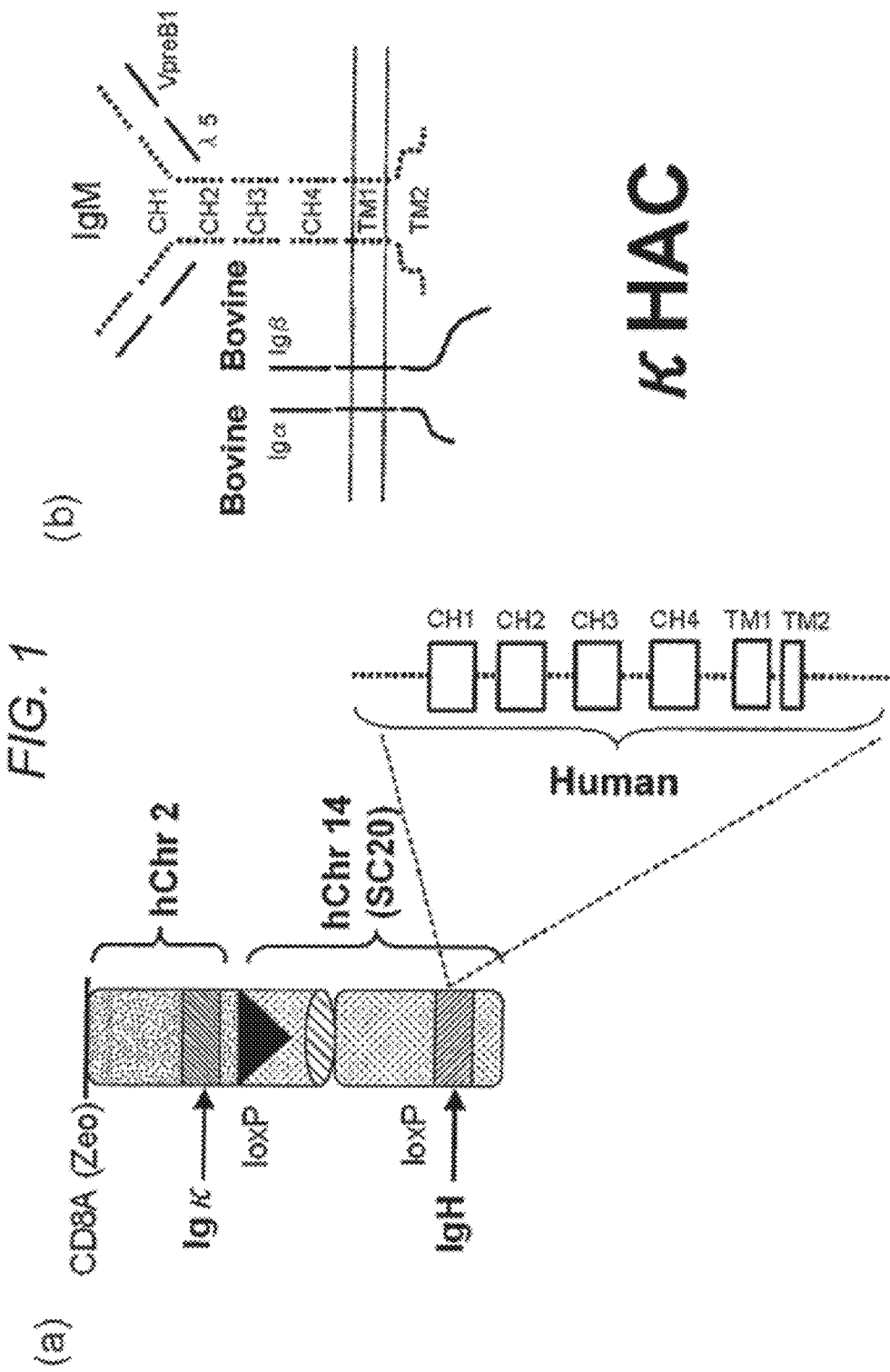
FIG. 1(a) illustrates a schematic view of κHAC.
FIG. 1(b) illustrates a schematic view of an IgM to be formed on a B cell membrane when κHAC is introduced into an animal.

The present invention relates to (1) a human artificial chromosome vector comprising a human antibody heavy chain gene, a human antibody light chain gene, and, a non-human animal-derived IgM heavy chain constant region gene, (2) an animal having the human artificial chromosome vector, and (3) a method for producing a human antibody, comprising administering a target antigen into the animal to produce and accumulate the antigen-specific human antibody in the serum of the animal, and recovering the antigen-specific human antibody from the serum.

1. The Human Artificial Chromosome Vector of the Present Invention

In the present invention, "the human artificial chromosome vector" refers to a vector which comprises a human chromosome-derived centromere sequence, a telomere sequence, and a replication origin and exists independently from a chromosome of a host cell in a nucleus of the host cell.

Specifically, the vector refers to a human artificial chromosome (HAC) vector prepared by translocating a desired region on the human chromosome into a stable human chromosome fragment.

Specific examples of a method for preparing a HAC include a method comprising: inserting a telomere sequence and a sequence loxP recognized by a Cre recombinant enzyme such that a desired region on a human chromosome or a chromosome fragment may be included, and binding a region inserted between the telomere sequence of the chromosome or the chromosome fragment and the loxP sequence to a region inserted between a telomere sequence on another chromosome or chromosome fragment (preferably a chromosome fragment which is stable in the nucleus and has a high transmission efficiency to progeny) and the loxP sequence by translocation (Kuroiwa et al., *Nature Biotechnology*, 18, 1086-1090, 2000 and WO No. 00/10383).

(Human Antibody Heavy Chain Gene)

The human artificial chromosome vector of the present invention comprises a human antibody heavy chain gene. In the present invention, "the human antibody heavy chain gene" refers to a gene which, among two identical heavy chains and two identical light chains constituting a human immunoglobulin molecule, encodes the former.

Specific examples of the human antibody heavy chain gene include a gene encoding a variable region of the heavy chain and genes encoding the γ chain, μ chain, α chain, δ chain, and ε chain which determine the structure of the constant region.

In the artificial chromosome vector of the present invention, "comprising the human antibody heavy chain gene" refers to comprising a DNA encoding the human antibody heavy chain gene. The human artificial chromosome vector of the present invention may be prepared by inserting a DNA encoding the human antibody heavy chain gene into any position or inserting or ligating a chromosome fragment comprising a DNA encoding the human antibody heavy chain gene.

The variable region gene and the constant region gene of the human antibody heavy chain form a cluster and is positioned at 14q32 on the human chromosome 14. Therefore, the artificial chromosome vector of the present invention preferably comprises a human chromosome 14 fragment, more preferably a human chromosome 14 fragment at which the variable region gene and the constant region gene of the human antibody heavy chain are positioned, and further preferably a human chromosome 14 fragment comprising the 14q32 region.

(Human Antibody Light Chain Gene)

The human artificial chromosome vector of the present invention comprises a human antibody light chain gene. In the present invention, "the human antibody light chain gene" refers to a gene that, among two identical heavy chains and two identical light chains constituting a human immunoglobulin molecule, encodes the latter.

Specific examples of the human antibody light chain gene include two types of genes, i.e., the κ chain gene and the λ chain gene. The gene of each chain comprises a gene encoding a variable region and a gene encoding a constant region.

The human artificial chromosome vector of the present invention may comprise either κ chain gene or the λ chain gene only, or both of the genes as the human antibody light chain gene.

In the human artificial chromosome vector of the present invention, "comprising the human antibody light chain gene" refers to comprising a DNA encoding the human antibody light chain gene. The human artificial chromosome vector of the present invention may be prepared by inserting a DNA encoding the human antibody light chain gene into any position or inserting or ligating a chromosome fragment comprising a DNA encoding the human antibody light chain gene.

The variable region gene and constant region of the κ chain and the λ chain forms a cluster to be positioned on a chromosome. The κ chain gene cluster is positioned at 2p11.2 of the human chromosome 2 (Gottfrie et al., *Genomics*, 16. 512-514, 1993) and the λ chain gene cluster is positioned at 22q11.2-12 of the human chromosome 22 (Collins et al., *Nature*, 377, 367-379, 1995).

Therefore, the artificial chromosome vector of the present invention preferably comprises a human chromosome 2 fragment, more preferably a human chromosome 2 fragment at which the κ chain gene cluster is positioned, and even more preferably a human chromosome 2 fragment comprising the 2p11.2-12 region.

In addition, the artificial chromosome vector of the present invention preferably comprises a human chromosome 22 fragment, more preferably a human chromosome 22 fragment at which the λ chain gene cluster is positioned, and even more preferably a human chromosome 22 fragment comprising the 22q11.2 region.

(IgM Heavy Chain Constant Region Gene)

The human artificial chromosome vector of the present invention comprises a non-human animal-derived IgM heavy chain constant region gene. The non-human animal is not particularly limited so long as the animal is a non-human animal which can be a host into which the human artificial chromosome vector of the present invention is introduced, and may be any of ungulates such as cows, horses, goats, sheep, and pigs; rodents such as mice, rats, and rabbits; poultry such as chickens, domestic ducks, and geese.

The non-human animal is preferably a non-human mammalian animal, more preferably an ungulate animal, and furthermore preferably a bovine.

In the present invention, "the IgM heavy chain constant region gene" refers to a gene encoding the IgM heavy chain constant region. The IgM heavy chain constant region promotes the generation of the B cell by interacting with the B cell membrane molecule Igα/Igβ to cause a signal transduction in cells. Specific examples of the IgM heavy chain constant region gene include genes encoding constant region domains such as CH1, CH2, CH3, and CH4, and the B-cell transmembrane domains such as TM1 and TM2.

The IgM heavy chain constant region gene derived from a non-human animal which is comprised in the human artificial chromosome vector of the present invention is not particularly limited so long as the region is in a range which may sufficiently induce the signal of the B cell generation in the above-described IgM heavy chain constant region, but preferably comprises TM1 domain and TM2 domain derived from a non-human animal, and more preferably genes encoding CH2 domain, CH3 domain, CH4 domain, TM1 domain, and TM2 domain which are derived from a non-human animal.

In the human artificial chromosome vector of the present invention, "comprising the non-human animal-derived IgM heavy chain constant region gene" refers to comprising a DNA encoding a non-human animal-derived IgM heavy chain constant region gene.

The human artificial chromosome vector of the present invention may be prepared by inserting a DNA encoding IgM heavy chain constant region gene derived from a non-human animal into any position, or ligating a chromosome fragment comprising a DNA encoding a human IgM heavy chain constant region gene.

In particular, it is preferred that some of the DNA encoding the human IgM heavy chain constant region gene on the human artificial chromosome is substituted with some of the DNA encoding the non-human animal-derived IgM heavy chain constant region gene.

Specifically, when a part of the DNA encoding the human IgM heavy chain constant region gene on the human artificial chromosome is substituted with a part of the DNA encoding IgM heavy chain constant region gene derived from a non-human animal, the DNAs encoding the TM1 domain and the TM2 domain in the human IgM heavy chain constant region gene on the human artificial chromosome are preferably substituted with the DNAs encoding the TM1 domain and the TM2 domain in the non-human IgM heavy chain constant region gene, respectively; and more preferably the DNAs encoding the CH1 domain, the CH2 domain, the CH3 domain, the CH4 domain, the TM1 domain, and the TM2 domain in the human IgM heavy chain constant region gene are substituted with the DNAs encoding the CH1 domain the CH2 domain, the CH3 domain, the CH4 domain, the TM1 domain, and the TM2 domain in the non-human IgM heavy chain constant region gene, respectively; or the DNAs encoding the CH2 domain, the CH3 domain, the CH4 domain, the TM1 domain, and the TM2 domain in the human IgM heavy chain constant region gene on the human artificial chromosome are substituted with the DNAs encoding the CH2 domain, the CH3 domain, the CH4 domain, the TM1 domain, and the TM2 domain of the non-human IgM heavy chain constant region gene, respectively.

The IgM heavy chain constant region gene derived from a non-human animal is preferably the IgM heavy chain constant region gene of a non-human mammalian animal, more preferably the IgM heavy chain constant region gene of an ungulate animal, and furthermore preferably the IgM heavy chain constant region gene of a bovine.

The IgM heavy chain constant region gene of the bovine is preferably a gene encoding a bovine IgM heavy chain constant region which is included in an IGHM region at which a bovine endogenous IgM heavy chain gene is positioned (derived from IGHM) or a gene encoding a bovine IgM heavy chain constant region in an IGHML1 region (derived from IGHML1), and more preferably a gene encoding a bovine IgM heavy chain constant region which is included in the IGHM region.

(Human Antibody Surrogate Light Chain Gene)

The human artificial chromosome vector of the present invention comprises a human antibody surrogate light chain gene. In the present invention, "the human antibody surrogate light chain gene" refers to a gene encoding an imaginary antibody light chain which is associated with an antibody heavy chain produced by a gene reconstitution in the human pro-B cell to constitute the pre-B cell receptor (preBCR).

Specific examples of the human antibody surrogate light chain gene include the VpreB gene and the λ5 gene. The human artificial chromosome vector of the present invention preferably comprises the VpreB gene and the λ5 gene as a human antibody surrogate light chain gene.

The VpreB gene of the present invention preferably comprises either or both of the VpreB 1 gene and the VpreB3 gene and more preferably both of the VpreB 1 gene and the VpreB3 gene.

In the human artificial chromosome vector of the present invention, "comprising the human antibody surrogate light chain gene" refers to comprising a DNA encoding the human antibody surrogate light chain gene. The human artificial chromosome vector of the present invention may be prepared by inserting a DNA encoding the human antibody surrogate light chain gene into any position or inserting or ligating a chromosome fragment comprising a DNA encoding the human antibody surrogate light chain gene.

Any of the VpreB gene and the AS gene is positioned within the human antibody λ chain gene locus at 22q11.2 of the human chromosome 22. Therefore, the human artificial chromosome vector of the present invention preferably comprises the human chromosome 22, more preferably the human chromosome 22 comprising the VpreB gene and the λ5 gene, and furthermore preferably the human chromosome 22 comprising the 22q11.2 region.

2. Method of Constructing a Human Artificial Chromosome Vector of the Present Invention The human artificial chromosome vector comprising the human antibody heavy chain gene, the human antibody light chain gene, and the human antibody surrogate light chain gene of the present invention may be constructed by using the following (1) to (3) methods.

(1) Construction of a Human Artificial Chromosome Fragment Comprising a Human Antibody Heavy Chain Gene The human artificial chromosome fragment comprising the human antibody heavy chain gene may be constructed by isolating the human chromosome 14 from a human normal cell to obtain a chromosome fragment comprising a human antibody heavy chain gene from the chromosome in accordance with a method described in WO98/037757.

Specifically, although a chromosome fragment which is incidentally generated during an isolation process of the human chromosome 14 or a process of maintaining the chromosome in a cell may be isolated by a method described in WO00/010383, a chromosome fragment may be obtained by irradiating an ionized radiation on the human chromosome 14 to break the chromosome, and a chromosome fragment may be also obtained by inserting a telomere sequence into a desired position of the human chromosome 14 to generate a deletion at the position.

Further, the thus obtained human artificial chromosome vector may be constructed by inserting or ligating a human chromosome fragment which does not comprise the human antibody heavy chain gene into a fragment comprising the human chromosome 14-derived human antibody heavy chain gene by using a method by Kuroiwa et al. (Kuroiwa et al., *Nature Biotechnology*, 18, 1086-1090, 2000 and WO00/010383).

Examples of the human artificial chromosome fragment comprising the human antibody heavy chain gene include SC20 (Tomizuka et al., *Proceeding of the National Academy of Sciences*, 97, 722-727, 2000 and WO98/037757), λHAC (Kuroiwa et al., *Nature Biotechnology*, 18, 1086-1090, 2000 and WO00/010383), κHAC (Kuroiwa et al., *Nature Biotechnology*, 27, 173-181, 2009 and WO09/111,086), ΔHAC and ΔΔHAC (Kuroiwa et al., *Nature Biotechnology*, 18, 1086-1090, 2000 and WO00/10383), and the like.

(2) Construction of an Artificial Chromosome Fragment Comprising a Human Antibody Light Chain Gene The human artificial chromosome fragment comprising the human antibody κ chain gene may be constructed by isolating the human chromosome 2 from a human normal cell to obtain a chromosome fragment comprising a human antibody κ chain gene from the chromosome in accordance with a method described in WO98/037757.

Specifically, although a chromosome fragment which is incidentally generated during the isolation process of the human chromosome 2 or the process of maintaining the chromosome in a cell may be isolated by a method described in WO00/010383, a chromosome fragment may be obtained by irradiating an ionized radiation on the human chromosome 2 to break the chromosome, and a chromosome fragment may also be obtained by inserting a telomere sequence into a desired position of the human chromosome 2 to generate a deletion at the position.

A human artificial chromosome fragment comprising the human antibody κ chain gene may be constructed by inserting or ligating a fragment comprising the human antibody κ chain gene derived from the human chromosome 2 into a human chromosome fragment which does not comprise the human antibody κ chain gene derived from the human chromosome 2 by using a method by Kuroiwa et al. (Kuroiwa et al., *Nature Biotechnology*, 27, 173-181, 2009 and WO09/111,086).

Examples of the human artificial chromosome fragment comprising the human antibody κ chain gene to be thus obtained include κHAC (Kuroiwa et al., *Nature Biotechnology*, 27, 173-181, 2009 and WO09/111,086).

The human artificial chromosome fragment comprising the human antibody λ, chain gene may be constructed by isolating the human chromosome 22 from a human normal cell to obtain a chromosome fragment comprising a human antibody λ chain gene from the chromosome in accordance with a method described in WO98/037757.

Specifically, although a chromosome fragment which is incidentally generated during the isolation process of the human chromosome 22 or the process of maintaining the chromosome in a cell may be isolated by a method described in WO00/010383, a chromosome fragment may be obtained by irradiating an ionized radiation on the human chromosome 22 to break the chromosome, and a chromosome fragment may also be obtained by inserting a telomere sequence into a desired position of the human chromosome 22 to generate a deletion at the position.

Further, a human artificial chromosome fragment comprising the human antibody λ, chain gene may be constructed by inserting or ligating a fragment comprising the human antibody λ chain gene derived from the human chromosome 22 into a human chromosome fragment which does not comprise the human antibody λ chain gene by using a method of Kuroiwa et al. (Kuroiwa et al., *Nature Biotechnology*, 18, 1086-1090, 2000 and WO00/010383.

Examples of the thus obtained human artificial chromosome fragment comprising the human antibody heavy chain gene include λHAC (Kuroiwa et al., *Nature Biotechnology*, 18, 1086-1090, 2000 and WO00/010383), ΔHAC and ΔΔHAC (Kuroiwa et al., *Nature Biotechnology*, 20, 889-894, 2002 and WO02/092812).

(3) Construction of a Human Artificial Chromosome Fragment Comprising a Non-Human Animal-Derived IgM Heavy Chain Constant Region Gene The non-human animal-derived IgM heavy chain constant region gene may be comprised into a human artificial chromosome vector of the present invention by substituting the human IgM heavy chain constant region gene on the human artificial chromosome fragment comprising the human antibody heavy chain gene which is constructed by the method of the above (1) with a non-human animal-derived IgM heavy chain constant region gene.

Specifically, the non-human animal-derived IgM heavy chain constant region gene may be constructed by substituting the DNAs encoding the CH2 domain, the CH3 domain, the CH4 domain, the TM1 domain, and the TM2 domain in the human IgM heavy chain constant region gene on the human artificial chromosome vector comprising the human antibody heavy chain gene constructed by the method of the above (1) with the DNAs encoding the CH2 domain, the CH3 domain, the CH4 domain, the TM1 domain, and the TM2 domain of the non-human IgM heavy chain constant region gene, respectively, by homologous recombination Therefore, the human artificial chromosome vector comprising the human antibody heavy chain gene, the human antibody light chain gene, and the non-human animal-derived IgM heavy chain constant region gene may be constructed by substituting the DNAs encoding the CH2 domain, the CH3 domain, the CH4 domain, the TM1 domain, and the TM2 domain in the human IgM heavy chain constant region gene on the human artificial chromosome fragment, comprising the human antibody heavy chain gene in the human artificial chromosome vector comprising the human antibody heavy chain gene and the human antibody light chain gene constructed by the methods of the above (1) or (2), with the DNAs encoding the CH2 domain, the CH3 domain, the CH4 domain, the TM1 domain, and the TM2 domain in the non-human IgM heavy chain constant region gene, respectively, by homologous recombination.

Alternately, the DNAs encoding the CH1 domain, the CH2 domain, the CH3 domain, the CH4 domain, the TM1 domain, and the TM2 domain in the human IgM heavy chain constant region gene on the human artificial chromosome fragment, comprising the human antibody heavy chain gene in the human artificial chromosome vector comprising the human antibody heavy chain gene and the human antibody light chain gene constructed by the methods of the above (1) to (3), with the DNAs encoding the CH1 domain, the CH2 domain, the CH3 domain, the CH4 domain, the TM1 domain, and the TM2 domain in the non-human IgM heavy chain constant region gene, respectively, by homologous recombination.

Further, the human artificial chromosome vector comprising a gene encoding the human antibody heavy chain, a gene encoding the human antibody light chain, and a gene encoding the non-human animal-derived IgM heavy chain constant region of the present invention may be constructed by using the methods of the above (1) to (3).

Specifically, the vector of the present invention may be constructed by substituting the human IgM heavy chain constant region gene on the human chromosome 14 fragment comprising the human antibody heavy chain gene constructed by the method of (1) with the non-human animal-derived IgM heavy chain constant region gene, and then ligating the human chromosome 2 fragment comprising the human κ chain gene constructed by the method of (2).

More specifically, a human artificial chromosome vector comprising the non-human animal-derived IgM heavy chain constant region gene of the present invention may be constructed in the following manner. The DNAs encoding the CH1 domain, the CH2 domain, the CH3 domain, the CH4 domain, the TM1 domain, and the TM2 domain in the human IgM heavy chain constant region gene on κHAC (Kuroiwa et al., *Nature Biotechnology*, 27, 173-181, 2009 and WO09/111, 086) are substituted with the DNAs encoding the CH1 domain, the CH2 domain, the CH3 domain, the CH4 domain, the TM1 domain, and the TM2 domain of the non-human IgM heavy chain constant region gene, respectively, by homologous recombination.

Figure 2:
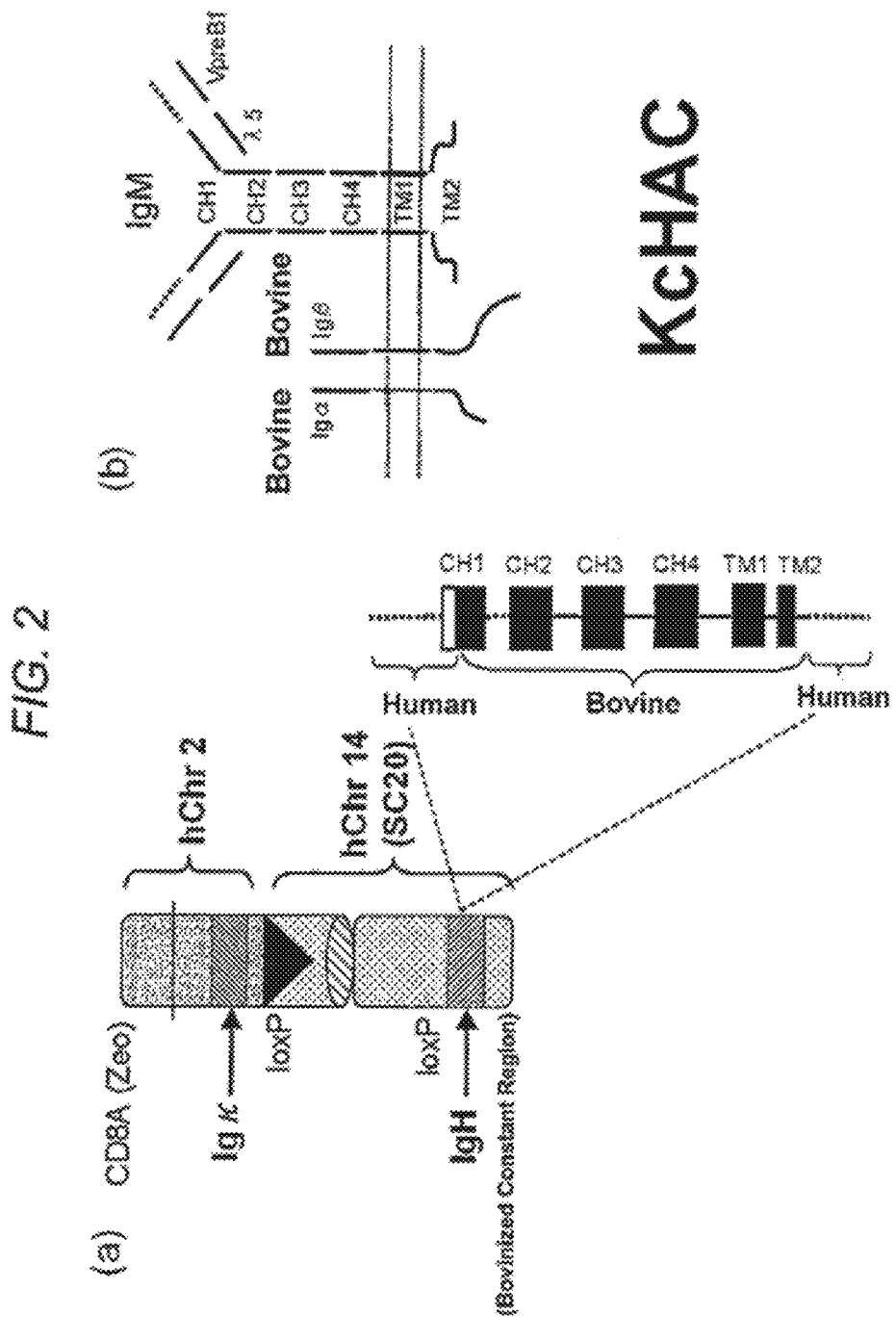
FIG. 2(a) illustrates a schematic view of KcHAC.
FIG. 2(b) illustrates a schematic view of an IgM to be formed on the B cell membrane when KcHAC is introduced into an animal.

Examples of the human artificial chromosome vector of the present invention to be constructed in this manner include KcHAC. In FIG. 2, a schematic view of KcHAC is shown. In FIG. 2, a schematic view of KcHAC is shown. As shown in FIG. 2, since KcHAC comprises a gene encoding a non-human animal (bovine)-derived IgM heavy chain constant region gene compared to the structure of κHAC (FIG. 1), it can be produce human antibodies with higher efficiency when it is introduced into an animal, and KcHAC may stably produce an animal which is capable of producing human antibodies with such a high efficiency.

(4) Construction of a Human Artificial Chromosome Fragment Comprising a Human Antibody Surrogate Light Chain Gene The human artificial chromosome fragment comprising the human antibody surrogate light chain gene may be constructed by isolating the human chromosome 22 from a human normal cell to obtain a chromosome fragment comprising a human antibody surrogate light chain gene from the chromosome in accordance with a method described in WO98/037757.

Specifically, although a chromosome fragment which is incidentally generated during the isolation process of the human chromosome 22 or the process of maintaining the chromosome in a cell may be isolated by a method described in WO00/010383, a chromosome fragment may be obtained by irradiating ionized radiation on the human chromosome 22 to break the chromosome, and a chromosome fragment may also be obtained by inserting a telomere sequence into a desired position of the human chromosome 22 to generate a deletion at the position.

Further, a human artificial chromosome fragment comprising the human antibody surrogate light chain gene may be constructed by inserting or ligating a fragment comprising the human antibody surrogate light chain gene into a human chromosome fragment which does not comprise the human antibody surrogate light chain gene by using a method of Kuroiwa et al. (Kuroiwa et al., *Nature Biotechnology*, 18, 1086-1090, 2000 and WO00/010383.

The human artificial chromosome vector comprising a gene encoding the human antibody heavy chain, a gene encoding the human antibody light chain, and a gene encoding the non-human animal-derived IgM constant region, and also comprising a gene encoding the human antibody surrogate light chain of the present invention may be constructed by using the methods of above (1) to (4).

Specifically, the vector of the present invention may be constructed by substituting the human IgM heavy chain constant region gene on the human chromosome 14 fragment comprising the human antibody heavy chain gene constructed by the method of (1) with the non-human animal-derived IgM heavy chain constant region gene by the method of (3); and then ligating the human chromosome 2 fragment comprising the human ιc chain gene constructed by the method of (2), and the human chromosome 22 fragment comprising the human chain gene and the human antibody surrogate light chain gene constructed by the methods of (2) and (4).

More specifically, a human artificial chromosome vector comprising the human antibody heavy chain gene, the human antibody light chain gene, and the human antibody surrogate light chain gene of the present invention, and also comprising the non-human animal-derived IgM constant region may be constructed in the following manner.

First, the DNAs encoding the DNAs encoding the CH2 domain, the CH3 domain, the CH4 domain, the TM1 domain, and the TM2 domain in the human IgM heavy chain constant region gene on the human chromosome 14 fragment are substituted with the DNAs encoding the CH2 domain, the CH3 domain, the CH4 domain, the TM1 domain, and the TM2 domain of the non-human IgM heavy chain constant region gene, respectively, by homologous recombination. Subsequently, a loxP sequence is inserted into the RNR2 gene locus (Worton et al., *Science*, 239, 64-68, 1988) on the human chromosome 14 fragment by homologous recombination.

Meanwhile, a loxP sequence and a lox2272 sequence which are recognition sequences of a Cre recombinant enzyme, are inserted into the cos138 site (Kuroiwa, *Nature Biotechnology*, 27, 173-181, 2009) which is positioned on the polar centromere side and into the AC 104134 site (Gene Accession No.) which is positioned on the polar telomere side of the human κ chain gene cluster region on the human chromosome 2 fragment, respectively, by homologous recombination.

Further, after a telomere sequence is inserted into the AP000350 site (Gene Accession No.) on the polar telomere side of a cluster region comprising the human λ chain gene and the human antibody surrogate light chain gene on the human chromosome 22 fragment by homologous recombination and then cut the chromosome, a lox 2272 sequence is inserted into the AP000553 site (Gene Accession No.) on the polar centromere side by homologous recombination.

By Cre/loxP recombination, both chromosomes are ligated by translocating the AP000553 site on the human chromosome 22 fragment into the AC104134 site on the human chromosome 2 fragment. In addition, by Cre/loxP recombination, three chromosomes are ligated by translocating the RNR2 gene locus on the human chromosome 14 fragment into the cos138 site on the human chromosome 2 fragment of the above ligated bodies.

Figure 3:
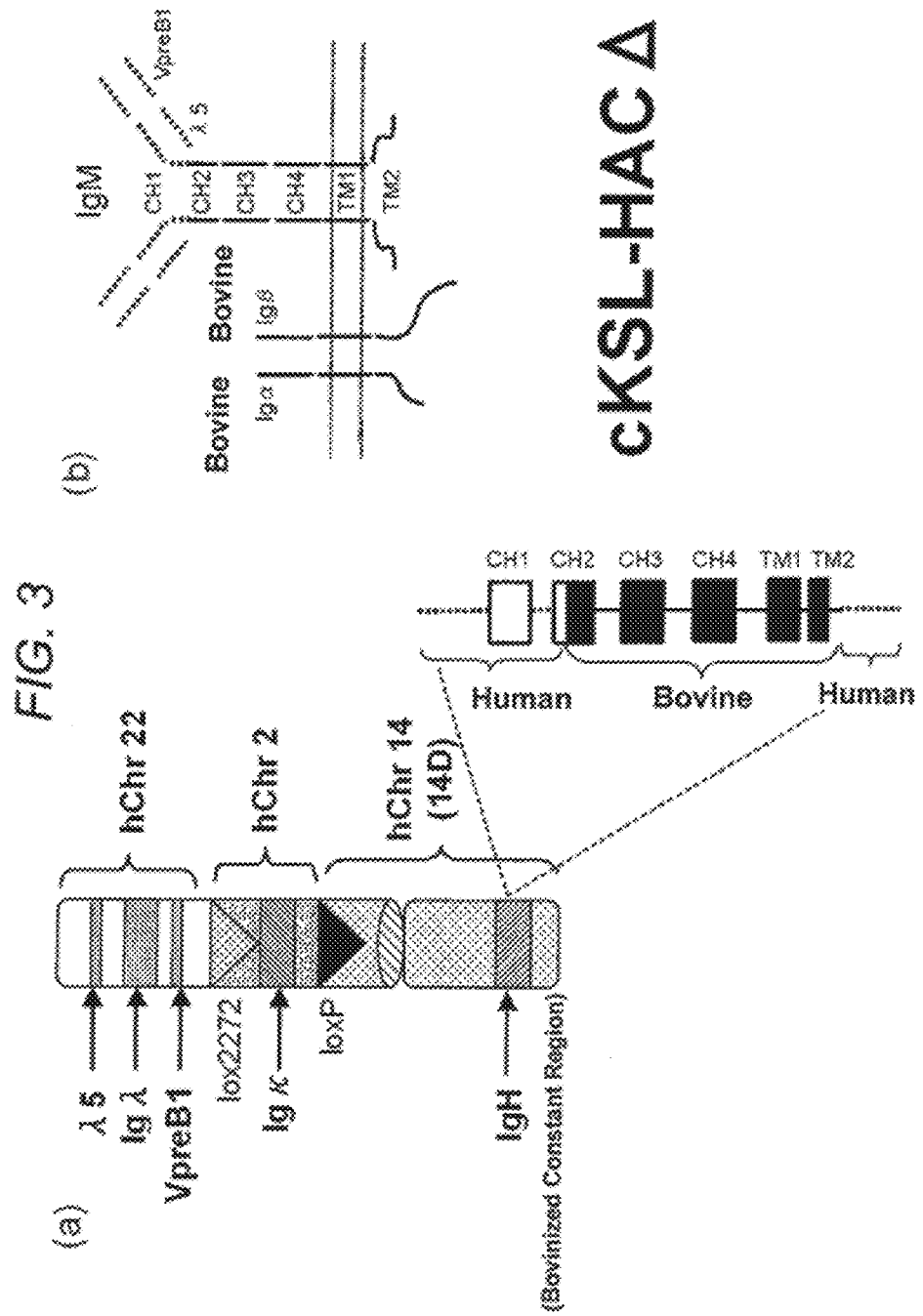
FIG. 3(a) illustrates a schematic view of cKSL-HACΔ.
FIG. 3(b) illustrates a schematic view of an IgM to be formed on the B cell membrane when cKSL-HACΔ is introduced into an animal.

Examples of the human artificial chromosome vector of the present invention to be constructed in this manner include cKSL-HACΔ. In FIG. 3, a schematic view of cKSL-HACΔ is shown. In FIG. 3, a schematic view of cKSL-HACΔ is shown. As shown in FIG. 3, since cKSL-HACΔ further comprises a gene encoding the non-human animal (bovine)-derived IgM heavy chain constant region and a gene encoding the human antibody surrogate light chain compared to the structure of κHAC (FIG. 1), it can be produce human antibodies with higher efficiency when it is introduced into an animal, and an animal which is capable of producing human antibodies with such a high efficiency may also be stably produced.

3. An Animal Having the Human Artificial Chromosome Vector of the Present Invention The animal having the human artificial chromosome vector of the present invention refers to an animal into which the human artificial chromosome vector of the present invention is introduced.

The animal having the human artificial chromosome of the present invention is not particularly limited so long as the animal is an animal in which the human artificial chromosome fragment may be introduced into a cell thereof, and any non-human animals, for example, ungulates such as cows, horses, goats, sheep, and pigs; rodents such as mice, rats, and rabbits; poultry such as chickens, domestic ducks, and geese; and the like may be used.

The non-human animal is preferably a non-human mammalian animal, more preferably an ungulate animal, and even more preferably a bovine.

An animal having the human artificial chromosome vector of the present invention may be constructed by introducing the human artificial chromosome vector of the present invention constructed by the method of the above (2) into an oocyte of a host animal.

Specifically, the human artificial chromosome vector of the present invention to be constructed by the method of the above (2) using the method described in WO2005/104835 and the method of Kuroiwa et al. (Kuroiwa et al., *Nature Biotechnology*, 20, 889-894) is introduced into a somatic cell derived from a host animal by a microcell fusion method. Thereafter, the animal having the human artificial chromosome vector may be constructed by transplanting a nucleus or chromatin agglomerate of the cell into an oocyte and transplanting the oocyte or an embryo to be formed from the oocyte into the uterus of a host animal to give birth.

It may be confirmed by a method of Kuroiwa et al. (Kuroiwa et al., *Nature Biotechnology*, 18, 1086-1090, 2000 and Kuroiwa et al., *Nature Biotechnology*, 20, 889-894) whether an animal constructed by the above method has the human artificial chromosome vector of the present invention.

4. Method for Producing a Human Antibody of the Present Invention

A antigen-specific human antibody may be produced by immunizing the animal having the human artificial chromosome vector of the present invention constructed in the above (3) with a desired antigen to produce the antigen-specific human antibody in the serum of the animal and recovering the antigen-specific human antibody from the serum.

The antigens for immunizing the animal having the human artificial chromosome vector of the present invention, are not particularly limited and examples include a tumor-associated antigen, an antigen associated with allergy or inflammation, an antigen associated with cardiovascular disease, an antigen associated with autoimmune disease, an antigen associated with neurodegenerative disease, and an antigen associated with viral or bacterial infections.

Examples of tumor-associated antigens include CD1a, CD2, CD3, CD4, CD5, CD6, CD7, CD9, CD10, CD13, CD19, CD20, CD21, CD22, CD25, CD28, CD30, CD32, CD33, CD38, CD40, CD40 ligand (CD40L), CD44, CD45, CD46, CD47, CD52, CD54, CD55, CD55, CD59, CD63, CD64, CD66b, CD69, CD70, CD74, CD80, CD89, CD95, CD98, CD105, CD134, CD137, CD138, CD147, CD158, CD160, CD162, CD164, CD200, CD227, adrenomedullin, angiopoietin related protein 4 (ARP4), aurora, B7-H1, B7-DC, integlin, bone marrow stromal antigen 2 (BST2), CA125, CA19.9, carbonic anhydrase 9 (CA9), cadherin, cc-chemokine receptor (CCR) 4, CCR7, carcinoembryonic antigen (CEA), cysteine-rich fibroblast growth factor receptor-1 (CFR-1), c-Met, c-Myc, collagen, CTA, connective tissue growth factor (CTGF), CTLA-4, cytokeratin-18, DF3, E-catherin, epidermal growth factor receptor (EGFR), EGFRvIII, EGFR2 (HER2), EGFR3 (HER3), EGFR4 (HER4), endoglin, epithelial cell adhesion molecule (Ep-CAM), endothelial protein C receptor (EPCR), ephrin, ephrin receptor (Eph), EphA2, endotheliase-2 (ET2), FAM3D, fibroblast activating protein (FAP), Fc receptor homolog 1 (FcRH1), ferritin, fibroblast growth factor-8 (FGF-8), FGF8 receptor, basic FGF (bFGF), bFGF receptor, FGF receptor (FGFR)$_3$, FGFR4, FLT1, FLT3, folate receptor, Frizzled homologue 10 (FZD10), frizzled receptor 4 (FZD-4), G250, G-CSF receptor, ganglioside (GD2, GD3, GM2, GM3, and the like), globo H, gp75, gp88, GPR-9-6, heparanase I, hepatocyte growth factor (HGF), HGF receptor, HLA antigen (HLA-DR, and the like), HM1.24, human milk fat globule (HMFG), hRS7, heat shock protein 90 (hsp90), idiotype epitope, insulin-like growth factor (IGF), IGF receptor (IGFR), interleukin (IL-6, IL-15, and the like), interleukin receptor (IL-6R, IL-15R, and the like), integrin, immune receptor translocation associated-4 (IRTA-4), kallikrein 1, KDR, KIR2DL1, KIR2DL2/3, KS1/4, lamp-1, lamp-2, laminin-5, Lewis y, sialyl Lewis x, lymphotoxin-beta receptor (LTBR), LUNX, melanoma-associated chondroitin sulfate proteoglycan (MCSP), mesothelin, MICA, Mullerian inhibiting substance type II receptor (MISIIR), mucin, neural cell adhesion molecule (NCAM), Necl-5, Notch1, osteopontin, platelet-derived growth factor (PDGF), PDGF receptor, platelet factor-4 (PF-4), phosphatidylserine, Prostate Specific Antigen (PSA), prostate stem cell antigen (PSCA), prostate specific membrane antigen (PSMA), Parathyroid hormone related protein/peptide (PTHrP), receptor activator of NF-kappaB ligand (RANKL), receptor for hyaluronic acid mediated motility (RHAMM), ROBO1, SART3, semaphorin 4B (SEMA4B), secretory leukocyte protease inhibitor (SLPI), SM5-1, sphingosine-1-phosphate, tumor-associated glycoprotein-72 (TAG-72), transferrin receptor (TfR), TGF-beta, Thy-1, Tie-1, Tie2 receptor, T cell immunoglobulin domain and mucin domain 1 (TIM-1), human tissue factor (hTF), Tn antigen, tumor necrosis factor (TNF), Thomsen-Friedenreich antigen (TF antigen), TNF receptor, tumor necrosis factor-related apoptosis-inducing ligand (TRAIL), TRAIL receptor (DR4, DR5, and the like), system ASC amino acid transporter 2 (ASCT2), trkC, TROP-2, TWEAK receptor Fn14, type IV collagenase, urokinase receptor, vascular endothelial growth factor (VEGF), VEGF receptor (VEGFR1, VEGFR2, VEGFR3, and the like), vimentin, VLA-4, and the like.

Examples of antigens associated with allergy or flare include IL-6, IL-6R, IL-5, IL-5R, IL-4, IL-4R, TNF, TNF receptor, CCR4, chemokine, chemokine receptor, and the like.

Examples of antigens associated with cardiovascular disease include GPIIb/IIIa, PDGF, PDGF receptor, blood coagulation factor, IgE, $\alpha_v\beta_3$, $\alpha_4\beta_7$, and the like.

Examples of antigens associated with viral or bacterial infections include gp120, CD4, CCR5, a verotoxin, an anthrax protective antigen, a methicillin-resistant *Staphylococcus aureus* (MRSA) antigen, a hepatitis type B virus (HBV) antigen, a cytomegalovirus (CMV) antigen, a Rabies antigen, a *Varicella zoster* antigen, and the like.

Other examples thereof include a T cell surface membrane protein mixtures, a Rh (D) antigen, crotalid venom, digoxin, and the like.

The immunization is carried out by administering the antigen with, for example, a complete Freund's adjuvant or an appropriate adjuvant such as an aluminum hydroxide gel, and pertussis bacteria vaccine, subcutaneously, intravenously, or intraperitoneally into an animal.

Examples of the form of administering the antigen into an animal having the human artificial chromosome vector of the present invention include peptides, protein, bacteria, viruses, cells, biological tissue pieces, and the like.

When the antigen is a partial peptide, a conjugate is produced with a carrier protein such as bovine serum albumin (BSA), keyhole Limpet hemocyanin (KLH) or the like, and is used as the immunogen.

The antigen is administered once to 10 times every 1 to 4 weeks after the first administration. After 1 to 14 days from each administration, blood is collected from the animal to measure the antibody value of the serum.

Examples of the method for detecting and measuring the antigen-specific human antibody included in the serum include a binding assay by an enzyme-linked immunosorbent assay [*Antibodies-A Laboratory Manual*, Cold Spring Harbor Laboratory (1988)], a biosensor Biacore, and the like.

Specifically, the binding amount of a human antibody in the serum may be measured by incubating the serum comprising the human antibody with antigen expressing cells, and then using an antibody specifically recognizing a human antibody.

Further, in addition to these methods, the antibody may be selected by identifying a target antigen of the antibody according to a method known in the art (*The Prostate*, 67, 1163, 2007).

Examples of the method for recovering human antibodies from the serum include a method of purifying by adsorbing the human antibody on a protein A carrier, a protein G carrier, or a carrier on which the human immunoglobulin specific antibody is supported.

Further, methods used in purification of proteins, such as gel filtration, ion exchange chromatography, and ultrafiltration, may be combined.

A human antibody produced by the above method may be a polyclonal antibody or a monoclonal antibody, and preferably a polyclonal antibody.

EXAMPLE

Example 1

Construction of a Targeting Vector
(1) Construction of a Targeting Vector pTEL'hisDpuro$^{lox2272}$F9R9

Methods described in the publication (Kuroiwa et al., *Nat. Biotechnol.* 18: 1086-1090, 2000, Kuroiwa et al., *Nat. Biotechnol.* 20: 889-894, 2002 and Kuroiwa et al., *Nat. Biotechnol.* 27: 173-181, 2009) were basically used for construction of a targeting vector.

Specifically, a genomic DNA fragment Dk-F9R9 used as a homology arm was amplified by PCR consisting of 40 cycles of 98° C. for 10 seconds and 68° C. for 9 minutes by using two primer DNAs of kD-F9 (5'-tcgaggatccgccagggagacagatgc-caagtacggtttag-3') (SEQ ID NO:1) and kD-R9 (5'-tcgaggatc-caggatctttgggggactgaatggggtgtgct-3') (SEQ ID NO:2) and a genomic DNA of a chicken DT40 cell line KTL1 (Kuroiwa et al., *Nat. Biotechnol.* 27: 173-181, 2009) having the human chromosome 2 as a template.

Subsequently, the plasmid pTEL'hisDpuro$^{lox2272}$ was constructed in the following order.

First, the plasmid pPUR$^{lox2272}$ was constructed by annealing two oligo DNA fragments [a DNA fragment consisting of a nucleotide sequence of 5'-agcttggatccataacttcgtatag-gatactttatacgaagttata-3' (SEQ ID NO:3) and a DNA fragment consisting of a nucleotide sequence of 5'-agcttataacttcg-tataaagtatcctatacgaagttatggatcca-3' (SEQ ID NO:4)] comprising a modified type lox2272 sequence, followed by cloning into the HindIII site of the plasmid pPUR (BD Bioscience Clontech).

Meanwhile, the plasmid pTEL'hisDPm was constructed by substituting the puromycin resistance gene (hereinafter referred to as puro$^r$) of the plasmid pTELpuro (Kuroiwa et al., *Nat. Biotechnol.* 18: 1086-1090, 2000, Kuroiwa et al., *Nat. Biotechnol.* 20: 889-894, 2002, and Kuroiwa et al., *Nat. Biotechnol.* 27: 173-181, 2009) with the hisD gene, substituting the EcoRI site with the SrfI site, and substituting the SpeI site with the PmeI site.

After generating the BamHI-digested fragment of the pPUR$^{lox2272}$ blunt ended, the obtained fragment was cloned into the PmeI site of the pTEL'hisDPm and thus obtained plasmid was named as the pTEL'hisDpuro$^{lox2272}$.

Figure 4:
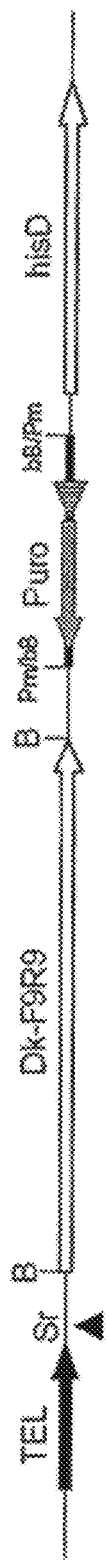
FIG. 4 illustrates a schematic view of a targeting vector pTEL'hisDpuro$^{lox2272}$F9R9.

The plasmid pTEL'hisDpuro$^{lox2272}$F9R9 was constructed by subcloning the Dk-F9R9 amplified by the above PCR into the BamHI site of the pTEL'hisDpuro$^{lox2272}$ (FIG. 4).

(2) Construction of a Targeting Vector pTELCAGzeoSLF2R2

In the same manner as in (1), the pTELCAGzeo(Sr)Pm was constructed by substituting the EcoRI site of the plasmid pTELpuro with the SrfI site, then substituting the SrfI site with the PmeI site, and further substituting the puro gene with the CAGzeo gene.

Meanwhile, a genomic DNA fragment used as a homology arm was amplified by repeating 40 cycles of 98° C. for 10 seconds and 68° C. for 9 minutes by using SL-F2 (5'-tcgag-gatccggcctcccaaaggattatagacgtgagccactgt-3') (SEQ ID NO:5) and SL-R2 (5'-tcgaggatccaaagaagggcccgc-ctctgcctctaaatcctgac-3') (SEQ ID NO:6) as a PCR primer set and a chromosome DNA of a chicken DT40 cell line 52-18 (Kuroiwa et al., *Nucleic Acids Res* 26: 3447-3448, 1998) having the human chromosome 22 as a template.

Figure 5:
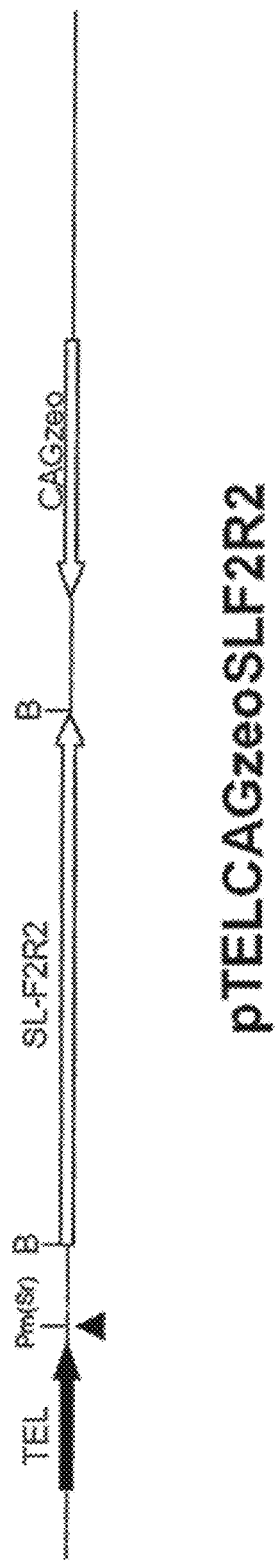
FIG. 5 illustrates a schematic view of a targeting vector pTELCAGzeoSLF2R2.

The pTELCAGzeoSLF2R2 was constructed by subcloning the PCR product obtained into the BamHI site of the plasmid pTELCAGzeo(Sr)Pm (FIG. 5).

(3) Construction of a Targeting Vector p553CAG$^{lox2272}$BsrDT

A vector having a structure in which a targeting vector pHCF2loxPHyg (Kuroiwa et al., *Nat. Biotechnol.* 18: 1086-1090, 2000) was substituted with the AP000553 site (GenBank accession Number) sequence in which a homology arm sequence of the HCF2 gene was amplified by PCR was constructed and used as the targeting vector p553loxPHyg(F).

At that time, the amplification of the AP000553 site fragment was carried out by PCR consisting of 40 cycles of 98° C. for 10 seconds and 68° C. for 15 minutes by using 553-F3 (5'-tgtagctgactttagccacccacaagtac-3') (SEQ ID NO:7) and 553-R3 (5'-cttgctgattatacctcatctccttccctc-3') (SEQ ID NO:8) as a primer set and a genomic DNA of the chicken DT40 cell 52-18 as a template.

After the obtained plasmid p553loxPHyg(F) was digested with NotI, a self-ligation was carried out, followed by cloning of the diphtheria toxin A fragment (hereinafter referred to as DT-A) into the Srf site.

Meanwhile, the pDRIVE-CAG (InvivoGen) was modified as follows. The oligo DNAs [5'-gtacaataacttcgtatagcatacat-tatacgaagttatagatctg-3' (SEQ ID NO:9) and 5'-aattcagatc-tataacttcgtataatgtatgctatacgaagttatt-3' (SEQ ID NO:10)] each comprising the loxP sequence were annealed and the lacZ fragment of the pDRIVE-CAG was substituted. The pCA-G$^{loxP}$ was constructed by cloning the fragment digested with SdaI and SwaI into the pBluescript SK-(Stratagene) digested with PstI and SmaI.

Subsequently, the loxP sequence of the pCAG$^{loxP}$ was substituted with a sequence comprising the lox2272 produced by annealing the two oligo DNAs [5'-gatctataacttcgtataggatactt-tatacgaagttatg-3' (SEQ ID NO:11) and 5'-ctagcataacttcg-tataaagtatcctatacgaagttata-3' (SEQ ID NO:12)]. Further, the pCAG$^{loxP2272}$bsr was constructed by inserting the blasticidin-resistance gene (bsr gene) into the SpeI site.

Figure 6:
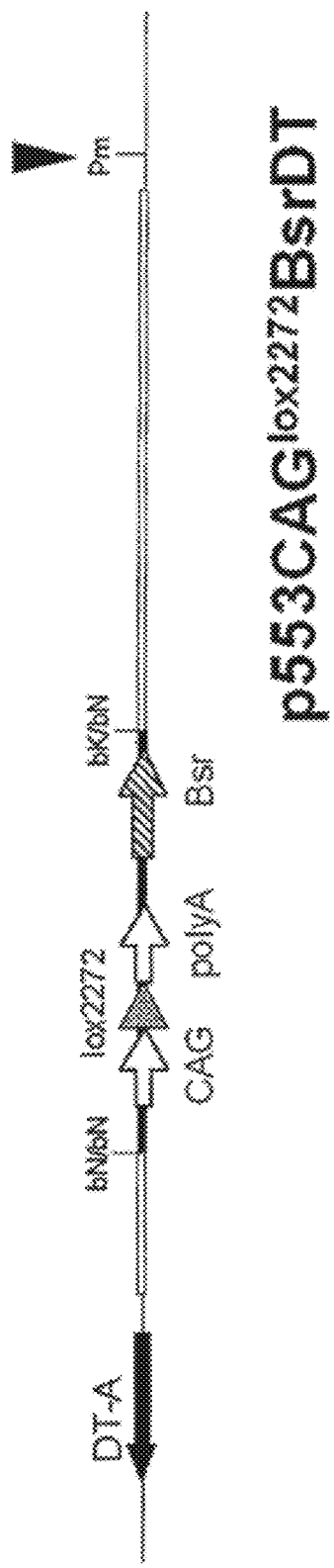
FIG. 6 illustrates a schematic view of a targeting vector p553CAG$^{lox2272}$BsrDT.

Finally, the p553CAG$^{lox2272}$BsrDT (FIG. 6) was completed by cloning the NotI-KpnI fragment (CAG-lox2272-polyA-bsr) into the NotI site.

(4) Construction of a Targeting Vector pSC355CAG$^{lox511}$hisDDT

A genomic DNA used as a homology arm was amplified by PCR consisting of 40 cycles of 98° C. for 10 seconds and 68° C. for 15 minutes by using SC355-F3 (5'-gtacaatcttggatcac-tacaacctctgcctacca-3') (SEQ ID NO:13) and SC355-R3 (5'-tgctgtgtctaatcaggtgttgaacccatctacta-3') (SEQ ID NO:14) as a primer set and a genomic DNA of the chicken DT40 cell comprising the human chromosome 14 as a template.

The KpnI site of the plasmid pBluescript was substituted with the SrfI site, and the DNA fragment amplified above was subcloned into the SpeI site. The obtained plasmid was used as the pSC355F3R3.

Subsequently, the loxP sequence of the pCAG$^{loxP}$ was substituted with a sequence comprising lox511 produced by annealing the two oligo DNAs [a DNA fragment consisting of the sequence 5'-gatctataacttcgtatagtatacattatacgaagttatg-3' (SEQ ID NO:15) and a DNA fragment consisting of the nucleotide sequence 5'-ctagcataacttcgtataatgtatac-tatacgaagttata-3' (SEQ ID NO:16)] and used as the pCA-G$^{lox511}$.

Figure 7:
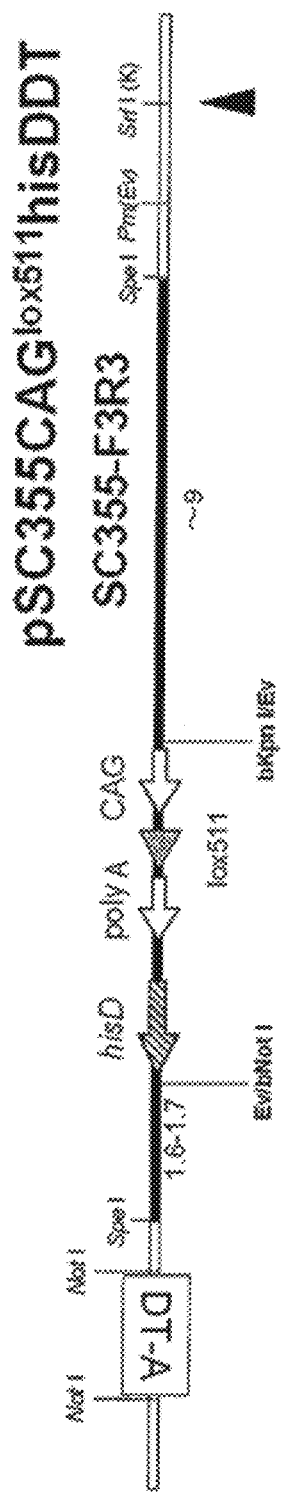
FIG. 7 illustrates a schematic view of a targeting vector pSC355CAG$^{lox511}$hisDDT.

The pCAG$^{lox511}$hisD was constructed by inserting the hisD gene into the SpeI site of the pCAG$^{lox511}$. A fragment (CAG-lox511-polyA-hisD) digested with NotI and KpnI was cloned into the EcoRV site of the pSC355F3R3. Finally, the plasmid obtained by subcloning the DT-A fragment into the NotI site was used as the pSC355CAG$^{lox511}$hisDDT (FIG. 7).

(5) Construction of a Targeting Vector p14CEN(FR) hygpuro$^{lox511}$DT A genomic DNA used as a homology arm was amplified by PCR consisting of 40 cycles of 98° C. for 10 seconds and 68° C. for 15 minutes by using 14 CEN-F (5'-tcgaggatccttcgccaccccaaagatgattacagattac-3') (SEQ ID NO:17) and 14 CEN-R (5'-tcgaggatcctacactagaagcacaaac-cccaccattacacat-3') (SEQ ID NO:18) as a primer set and a genomic DNA of the chicken DT40 cell comprising the human chromosome 14 as a template.

The p14CEN(FR) was constructed by subcloning the PCR product into the BamHI site of the pBluescript in which the KpnI site was substituted with the PmeI site.

The oligo DNAs [a DNA fragment consisting of a nucleotide sequence of 5'-agcttggatccataacttcgtatag-tatacattatacgaagttata-3' (SEQ ID NO:19) and a DNA fragment consisting of a nucleotide sequence of 5'-agcttataacttcgtataatgtatactatacgaagttatggatcca-3' (SEQ ID NO:20)] comprising the lox511 sequence were annealed. The plasmid pPUR$^{lox511}$ was constructed by cloning the fragment obtained into the HindIII site of the plasmid pPUR (BD Bioscience Clontech).

The pHygPuro$^{lox511}$ was constructed by cloning the BamHI-digested fragment of the pPUR$^{lox511}$ into the BamHI site of the pBluescript, and the hygromycin resistance gene (hyg gene) into the EcoRV site, respectively.

Figure 8:
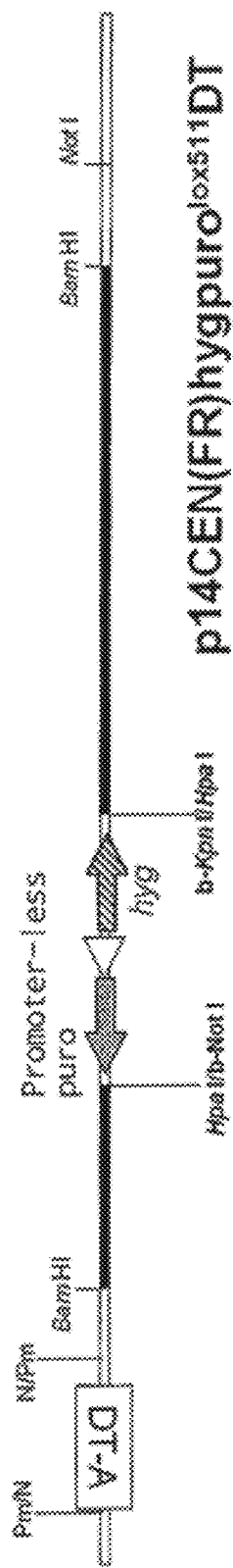
FIG. 8 illustrates a schematic view of a targeting vector p14CEN(FR) hygpuro$^{lox511}$DT.

A fragment (puro-lox511-hyg) digested with NotI and KpnI was cloned into the HpaI site of the p14CEN(FR). Finally, the p14CEN(FR)hygpuro$^{lox511}$DT (FIG. 8) was completed by subcloning the DT-A fragment into the PmeI site.

(6) Construction of a Targeting Vector pRNR2$^{loxP}$bsrDT

Figure 9:
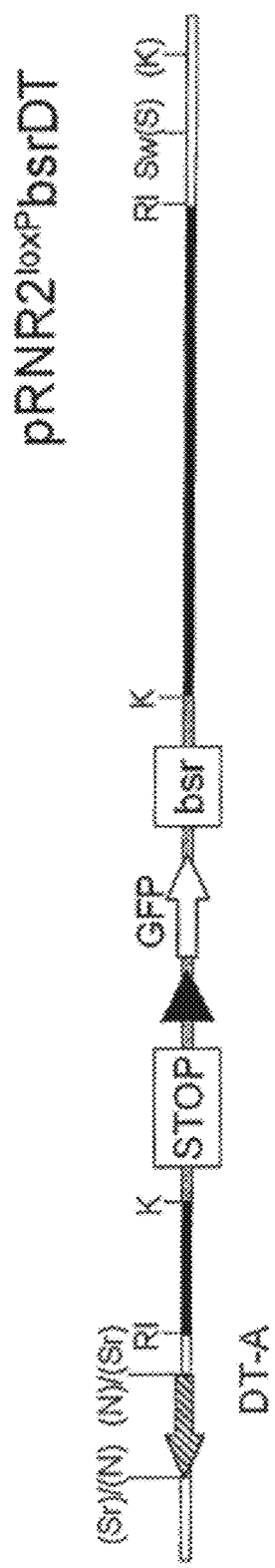
FIG. 9 illustrates a schematic view of a targeting vector pRNR2$^{loxP}$bsrDT.

The targeting vector pRNR2$^{loxP}$bsrDT (FIG. 9) was constructed by inserting the DT-A fragment into the vector pRNR2$^{loxP}$bsr (Kuroiwa et al., Nat. Biotechnol. 18: 1086-1090, 2000).

(7) Construction of a Targeting Vector pCH1CAGzeoDT

A λ phage genomic library of κHAC (WO2009/111086) was constructed from the CHO cell comprising κHAC by a Custom Library Construction Service (Loftstrand Labs, Ltd.) by using the λFIX II vector.

A clone comprising the human IgM constant region from the constructed genomic library was screened by using, as a probe, a PCR product amplified by PCR consisting of 40 cycles of 98° C. for 10 seconds, 64° C. for 30 seconds, and 72° C. for 1 minute with DNAs consisting of nucleotide sequences of 5'-cagtccccggcagattcaggtgtcc-3' (SEQ ID NO:21) and of 5'-gaaagtggcattggggtggctctcg-3' (SEQ ID NO:22) as a primer and a chromosome DNA extracted from the CHO cell (WO2009/111086) comprising κHAC as a template. As a result, clones #1, #4, and #7 were isolated.

Clone #4 (the PmlI fragment, 1.7 kb) was subcloned into the SmaI site of the pBluescript and was named as pCH1S(F). pCH1SSP(F) was constructed by subcloning the SacI-PmlI fragment (1 kb) derived from the plasmid pBCμAY37-95 in which the SalI-bovine IGHM chromosome fragment was cloned into the pBluescript, into the PstI site of pCH1S(F).

pCH1 SL was constructed by cloning the SmaI-EcoRI fragment (7.4 kb) derived from clone #1 into pCH1 SSP(F) digested with EcoRV/EcoRI.

Meanwhile, from the pBCμAY37-95, the SacI-digested fragment (3.5 kb) was pCH2S(F) was subcloned into the pBluescript. pmAYSazeo(F) was constructed by cloning the XhoI-digested fragment (the fragment constructed by inserting the CAGzeo fragment into the EcoRV site of pBS246 (Gibco) and digesting with XhoI) of CAGzeo into which the loxP sequence was introduced, into the Van91I site of the obtained plasmid.

Figure 10:
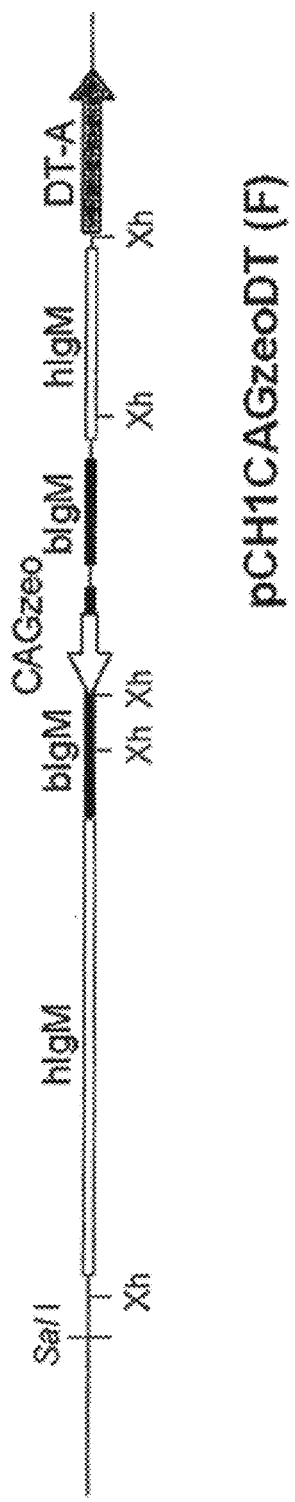
FIG. 10 illustrates a schematic view of a targeting vector pCH1CAGzeoDT.

Further, pCH1zeo(F) was constructed by subcloning the SacI fragment of pmAYSazeo(F) into the blunt-ended EcoRI site of pCH1SL. Finally, the pCH1CAGzeoDT (FIG. 10) was completed by subcloning the DT-A fragment into the NotI site of pCH1zeo(F).

(8) Construction of a Targeting Vector pCH2CAGzeoDT

The SeSp fragment produced by annealing the oligo DNAs consisting of nucleotide sequences of 5'-ggaccaggtggagact-gtgcagtcctcacccataactttcagggcctacagcatgctg-3' (SEQ ID NO:23) and 5'-cagcatgctgtaggccctgaaagt-tatgggtgaggactgcacagtctccacctggtcc-3' (SEQ ID NO:24) was cloned into the blunt-ended PstI site of pBluescript.

pmAYSpB was constructed by subcloning a fragment (about 2 kb) digested with SphI and BamHI from the plasmid pBCμAY37-95 into the SphI-BamHI site of the plasmid obtained above.

Similarly, the pmAYSpBPml was constructed by subcloning a fragment (about 2 kb) digested with BamHI and PmlI of the pBCμAY37-95 into the BamHI-PmlI site (with which the original SpeI site is substituted) of the pmAYSpB.

The pRISe was constructed by subcloning the EcoRI-SexAI fragment (about 0.6 kb) of clone #1 in Example 1(7) into the EcoRI-SexA1 site of the pmAYSpBPm.

Subsequently, the pRISeCAGzeo(R) was constructed by subcloning the CAGzeo into which the loxP sequence was introduced, into the Van91I site of the pRISe. Further, the pRISeCAGzeoE was constructed by substituting the NotI site of the pRISeCAGzeo(R) with the EcoRI site.

Meanwhile, the pCH2S(F) was constructed by subcloning the PmlI fragment (about 1.7 kb) of clone #4 in Example 1(7) into the SmaI site of the pBluescript in which the EcoRV site was substituted with the MluI site.

The pCH2LS was constructed by cloning a fragment (about 6.6 kb) digested with MluI and EcoRI of clone #1 in Example 1(7) into the MluI-EcoRI site of the pCH2S(F).

Figure 11:
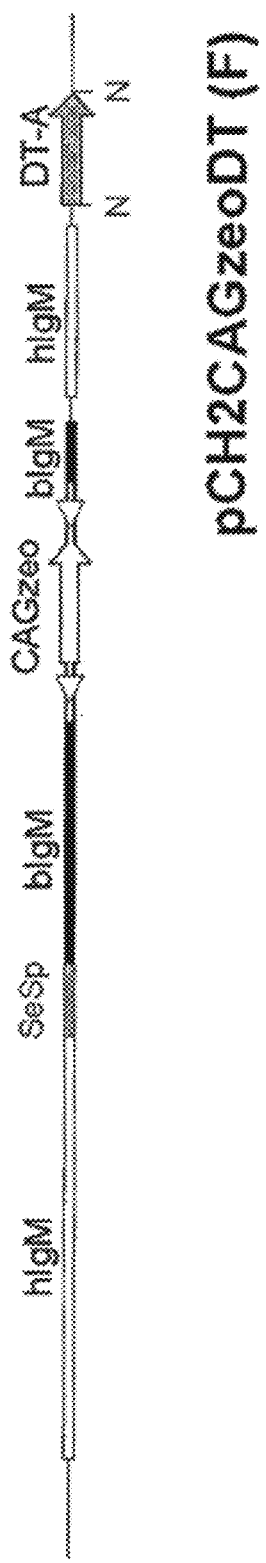
FIG. 11 illustrates a schematic view of a targeting vector pCH2CAGzeoDT.

Subsequently, the pCH2CAGzeo(F) was constructed by subcloning the EcoRI fragment of the pRISeCAGzeoE into the EcoRI site of the pCH2LS. Finally, the pCH2CAGzeoDT (FIG. 11) was completed by subcloning the DT-A fragment into the NotI site of the pCH2CAGzeo(F).

Example 2

Construction of KSL-HAC (1) Modification of the Human Chromosome 2 in a Chicken DT40 Cell In order to generate a deletion at the AP104134 site of the human chromosome 2 and insert a lox2272 sequence and a promoterless puro$^r$ cassette, the targeting vector pTEL'hisDpurolox2272F9R9 was linearized with SrfI (Stratagene) and introduced into KTL1 (Kuroiwa et al., *Nat. Biotechnol.* 27: 173-181, 2009) which was a chicken DT40 cell line having the human chromosome 2 fragment digested at the CD8A gene locus by electroporation (550 V, 25 µF). The electroporation of the DT40 cell was carried out by a method described in the publication (Kuroiwa et al., *Nat. Biotechnol.* 18: 1086-1090, 2000).

Colonies were subjected to selection by histidinol (0.5 mg/ml, Sigma) for two weeks and the sensitivity to puromycin (1 µg/ml, Sigma) was measured as an index of deletion of the puro$^r$ cassette on the CD8A gene locus. The chromosome DNA was extracted from a colony having the puromycin sensitivity by using the Gentra Puregene cell kit (QIAGEN), and was subjected to a PCR screening using the FABP1-F (5'-tatcaagggggtgtcggaaatcgtg-3') (SEQ ID NO:25) and the FABP1-R (5'-actgggcctgggagaacctgagact-3') (SEQ ID NO:26) as primers.

Figure 12:
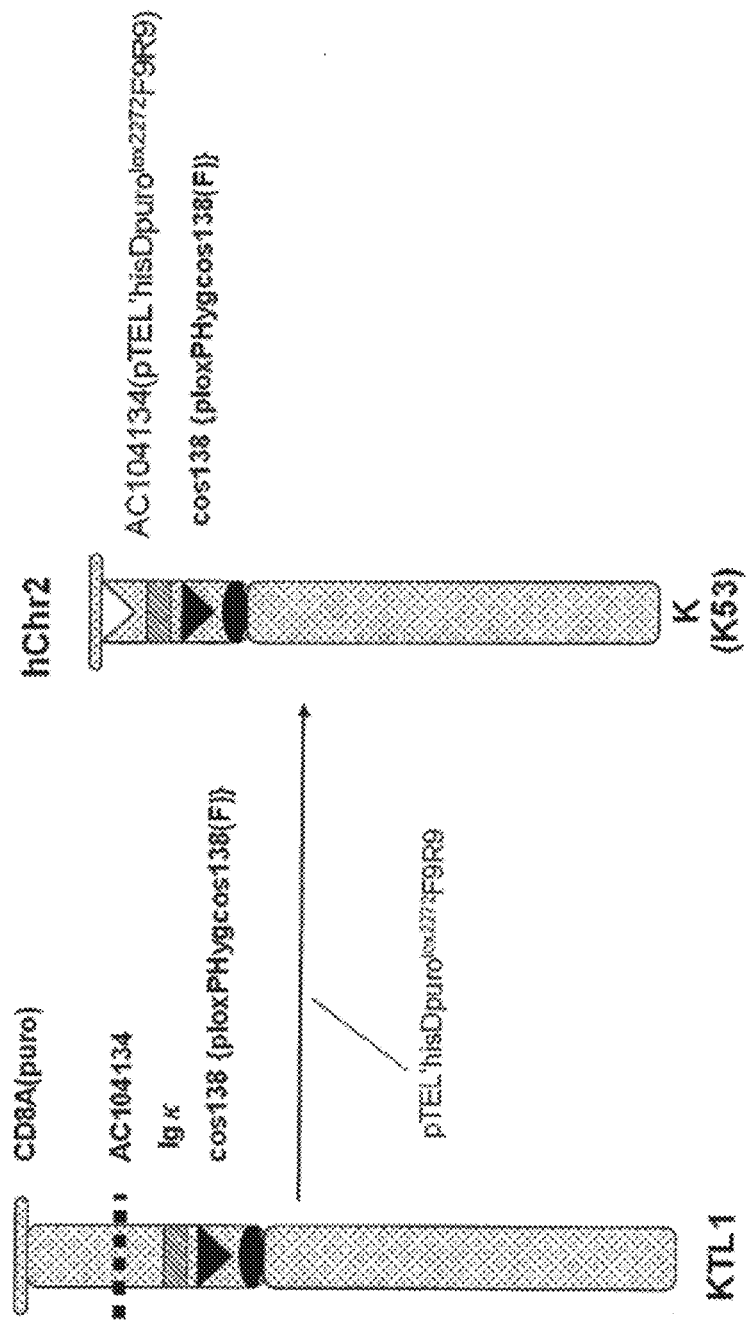
FIG. 12 illustrates an outline of a method for modifying the human chromosome 2 in a chicken DT40 cell.

PCR was carried out under a condition of amplifying the FABP 1 gene locus which was present in KTL1 but was not present at a target clone by repeating 30 cycles of 98° C. for 10 seconds, 60° C. for 30 seconds, and 72° C. for 1 minute. As a result, clone K53 was identified as a clone in which a desired deletion occurred. FIG. 12 illustrates an outline of a method for modifying the human chromosome 2 in a chicken DT40 cell.

(2) Modification of the Human Chromosome 22 in a Chicken DT40 Cell

In order to generate a deletion at the AP000350 site which is positioned on about 450 Mb telomere side from the AP000344 site (Kuroiwa et al., *Nat. Biotechnol.* 20: 889-894, 2002) of the human chromosome 22, the targeting vector pTELCAGzeoSLFR was linearized with PmeI (New England Biolabs) and introduced into 52-18 (Kuroiwa et al., *Nucleic Acids Res* 26: 3447-3448, 1998) which is a chicken DT40 cell line having the human chromosome 22 by electroporation (550 V, 25 µF).

A colony was subjected to selection by Zeocin (1 mg/ml, Invitrogen) for 2 weeks. A genomic DNA extracted from the thus obtained colony was subjected to PCR screening by using 350T-F (5'-gaggtgggctgaggggcaagtgtg-3') (SEQ ID NO:27) and 350T-R (5'-tacgaggaggggaggcagtgagagg-3') (SEQ ID NO:28) as primers.

PCR was carried out under conditions (repeating 30 cycles of 98° C. for 10 seconds, 63° C. for 30 seconds, and 72° C. for 1 minute) in which the AP000350 site which was present at 52-18 but was not present at a clone in which the targeting occurred, was amplified. As a result, it was found that a digestion was generated exactly in clone ST13.

In order to integrate a lox2272 sequence and a CAG promoter into the AP000553 site, the targeting vector p553CAGlox2272bsrDT which was linearized with PmeI (New England Biolabs) was introduced into ST13 by electroporation (550 V, 25 µF).

A colony was subjected to selection by blasticidin S (15 µg/ml, Invitrogen) for 2 weeks. A genomic DNA was extracted from the thus obtained colony and was subjected to PCR screening by using 553KO-F (5'-gtcagccaggcgggccatt-taccgtaagttatgta-3') (SEQ ID NO:29) and 553KO-R (5'-agggctgggttagatggcaccaaatgaaaggagaa-3') (SEQ ID NO:30) as primers.

Figure 13:
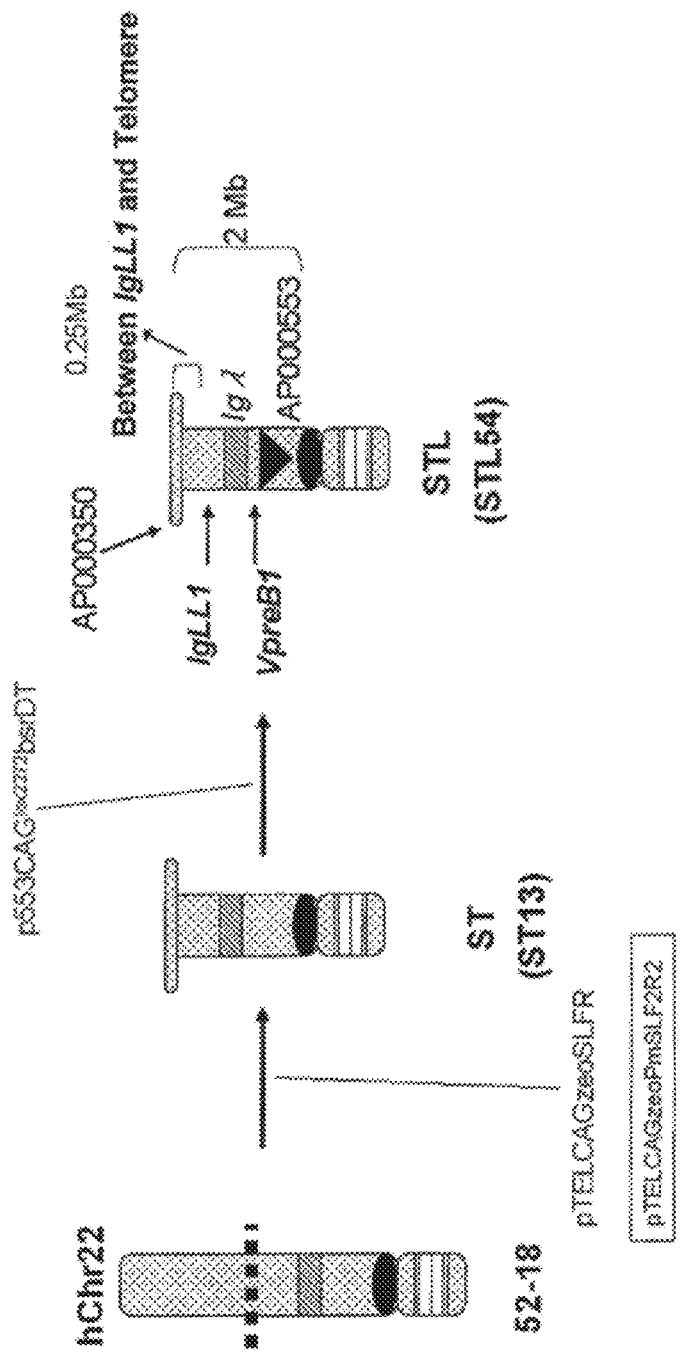
FIG. 13 illustrates an outline of a method for modifying the human chromosome 22 in a chicken DT40 cell.

PCR was carried out by repeating 40 cycles of 98° C. for 10 seconds and 68° C. at 6 minutes. As a result, clone STL54 was identified as a clone in which a targeting occurred. FIG. 13 illustrates an outline of a method for modifying the human chromosome 22 in a chicken DT40 cell.

(3) Construction of a SLKH Fragment in a DT40 Hybrid Cell

A SLKH fragment was constructed in a chicken DT40 hybrid cell according to a method of the publication (Kuroiwa et al., *Nat. Biotechnol.* 27: 173-181, 2009).

The K53 (Kuroiwa et al., *Nat. Biotechnol.* 27: 173-181, 2009) comprising a fragment derived from the human chromosome 2 having a hyg$^r$ cassette prepared in Example 2(1) and the STL54 comprising a fragment derived from the human chromosome 22 having a bs$^r$ cassette prepared in Example 2(2) were fused by using the PEG1500 (Roche) to prepare a DT40 hybrid cell.

The colony was maintained in the presence of hygromycin B (1.5 mg/ml, Invitrogen) and blasticidin S (20 µg/ml, Invitrogen) for 3 weeks to select a cell maintaining both human chromosome fragments. A genomic DNA was extracted from the colony and was subjected to PCR.

It was confirmed whether the human chromosome 2 fragment was maintained by carrying out PCR which repeated 40 cycles consisting of 98° C. for 10 seconds and 65° C. for 8 minutes when cos138KO-F and cos138KO-R were used and 40 cycles consisting of 98° C. for 10 seconds, 60° C. for 30 seconds, and 72° C. for 1 minute for other cases, respectively, using primer combinations shown in Table 1.

TABLE 1

Combinations of Primers for PCR

| | Primer | Nucleotide sequence of primer |
|---|---|---|
| PCR 1 | IGKC-F | 5'-tggaaggtggataacgcccct-3' (SEQ ID NO: 31) |
| | IGKC-R | 5'-tcattctcctccaacattagca-3' (SEQ ID NO: 32) |
| PCR 2 | IGKV-F | 5'-agtcagggcattagcagtgc-3' (SEQ ID NO: 33) |
| | IGKV-R | 5'-gctgctgatggtgagagtga-3' (SEQ ID NO: 34) |
| PCR 3 | RPIA-F | 5'-cttacccaggctccaggctctatt-3' (SEQ ID NO: 35) |
| | RPIA-R | 5'-ctctacctccctacccatcatcac-3' (SEQ ID NO: 36) |
| PCR 4 | EIF2AK3-F | 5'-aggtgctgctgggtggtcaagt-3' (SEQ ID NO: 37) |
| | EIF2AK3-R | 5'-gctcctgcaaatgtctcctgtca-3' (SEQ ID NO: 38) |
| PCR 5 | cos138KO-F | 5'-tctttctctcacctaattgtcctggc-3' (SEQ ID NO: 39) |
| | cos138KO-R | 5'-aggactggcactcttgtcgatacc-3' (SEQ ID NO: 40) |

It was confirmed whether the human chromosome 22 fragment was maintained by carrying out PCR by the following reaction cycle, for each case with a combination of primers shown in the following Table 2.

For each PCR reaction, PCR1 and 7 were carried out at 40 cycles of 98° C. for 10 seconds, 60° C. for 30 seconds, and 72° C. for 1 minute, PCR2 and 3 were carried out at 40 cycles of 98° C. for 10 seconds, 63° C. for 30 seconds, and 72° C. for 1 minute, PCR4 and 5 were carried out at 40 cycles of 98° C. for 10 seconds, 56° C. for 30 seconds, and 72° C. for 1 minute, PCR6 was carried out at 40 cycles of 98° C. for 10 minutes, 65° C. for 30 seconds, and 72° C. for 1 minute, and PCR8 was carried out at 40 cycles of 98° C. for 10 seconds and 68° C. for 6 minutes.

TABLE 2

Combinations of Primers for PCR

| | Primer name | Nucleotide sequence of primer |
|---|---|---|
| PCR 1 | 553P-F | 5'-agatctcttgagcccagcagtttga-3' (SEQ ID NO: 41) |
| | 553P-R | 5'-tgaagttagccggggatacagacg-3' (SEQ ID NO: 42) |
| PCR 2 | hVpreB1-F | 5'-tgtcctgggctcctgtcctgctcat-3' (SEQ ID NO: 43) |
| | hVpreB1-R | 5'-ggcggcggctccaccctctt-3' (SEQ ID NO: 44) |
| PCR 3 | hVpreB3-F | 5'-cactgcctgcccgctgctggta-3' (SEQ ID NO: 45) |
| | hVpreB3-R | 5'-gggcggggaagtgggggagag-3' (SEQ ID NO: 46) |
| PCR 4 | IgL-F | 5'-ggagaccaccaaaccctccaaa-3' (SEQ ID NO: 47) |
| | IgL-R | 5'-gagagttgcagaaggggtgact-3' (SEQ ID NO: 48) |
| PCR 5 | 344-F | 5'-atcatctgctcgctctctcc-3' (SEQ ID NO: 49) |
| | 344-R | 5'-cacatctgtagtggctgtgg-3' (SEQ ID NO: 50) |
| PCR 6 | hL5-F | 5'-agcccaagaacccagccgatgtga-3' (SEQ ID NO: 51) |
| | hL5-R | 5'-ggcagagggagtgtggggtgttgtg-3' (SEQ ID NO: 52) |
| PCR 7 | 350P-F | 5'-accagcgcgtcatcatcaag-3' (SEQ ID NO: 53) |
| | 350P-R | 5'-atcgccagcctcaccatttc-3' (SEQ ID NO: 54) |
| PCR 8 | 553KO-F | 5'-gtcagccaggcgggccatttaccgtaagttatgta-3' (SEQ ID NO: 55) |
| | 553KO-R | 5'-agggctgggttagatggcaccaaatgaaaggagaa-3' (SEQ ID NO: 56) |

Further, a fluorescence in situ hybridization (FISH) using the Human Cot-1 DNA (Invitrogen) as a probe was carried out according to a method in the publication (Kuroiwa et al., *Nat. Biotechnol.* 18: 1086-1090, 2000), and it was confirmed that two human chromosome fragments had appropriate sizes (the human chromosome 2 fragment was about 154 Mb and the human chromosome 22 fragment was about 24 Mb of). As a result, clone SLK2 was identified as a positive clone.

In order to cause a site specific recombination among two lox2272 sites, the AC104134 site on the human chromosome 2 fragment and the AP000553 site on the human chromosome 22 fragment, the Cre expression plasmid was introduced into SLK2 by electroporation (550 V, 25 μF).

A recombinant was selected in the presence of puromycin (1 to 5 μg/ml, Invitrogen) for 10 days by using the puromycin resistance imparted by the CAG promoter-lox2272-puro$^r$ cassette formed at the translocation position.

Further, it was confirmed that the recombination was occurred by PCR (40 cycles of 98° C. for 10 seconds and 68° C. for 1.5 minutes) using CAGpuro-F3 (5'-gcggcgccggcag-gaaggaaatg-3') (SEQ ID NO:57) and CAGpuro-R3 (5'-cgag-gcgcaccgtgggcagta-3') (SEQ ID NO:58) as primers and sequencing analysis of PCR products.

Figure 14:
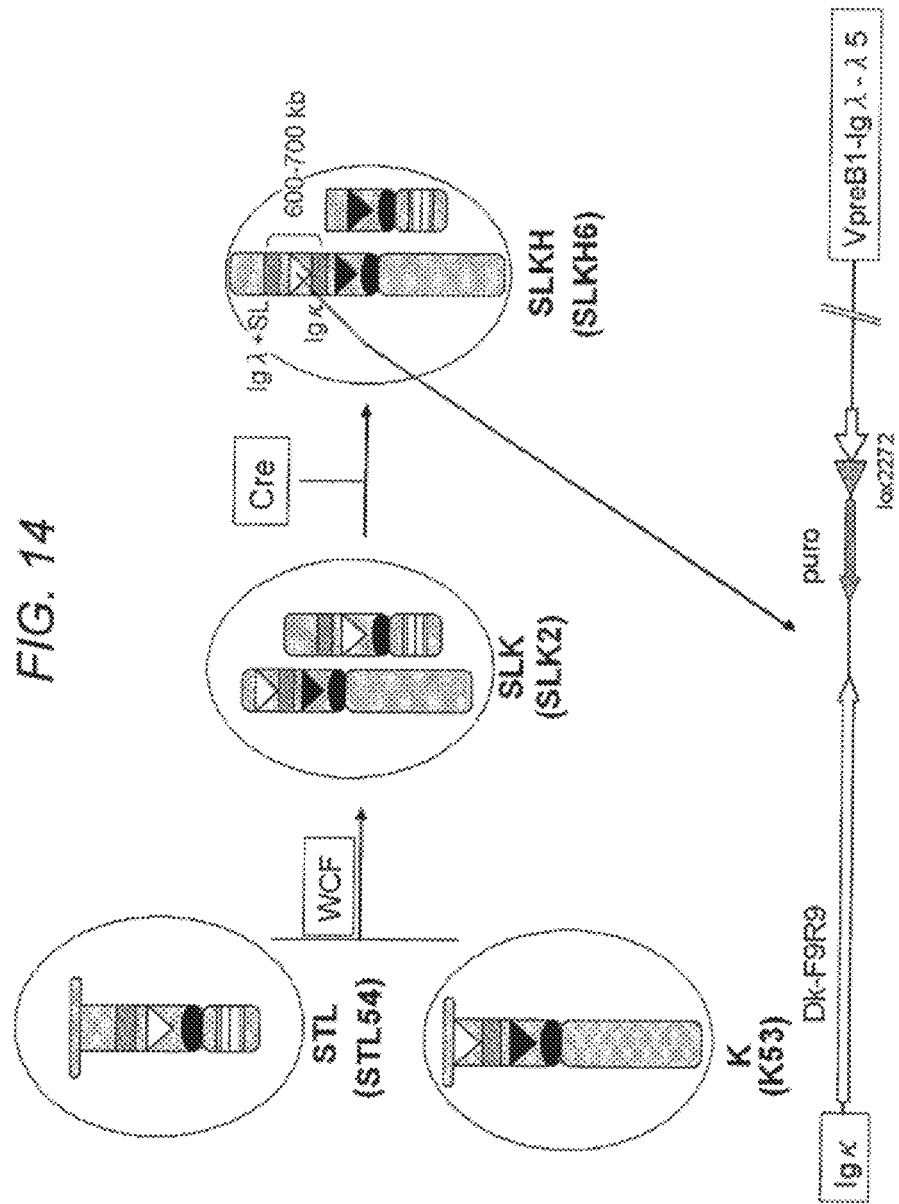
FIG. 14 illustrates an outline of a method for constructing the SLKH fragment in a DT40 hybrid cell.

As a result, SLKH6 was identified as a clone in which a desired translocation was occurred to maintain the SLKH fragment. FIG. 14 illustrates an outline of a method for constructing the SLKH fragment in a DT40 hybrid cell.

Example 3

Construction of CH2D (1) Modification 1 of the Human Chromosome 14 in a DT40 Cell In order to integrate a lox511 sequence and a CAG promoter on the AL512355 site which is positioned on the centromere side about 300 kb from the IgH gene locus, the targeting vector pSC355CAGlox511hisDDT linearized with SrfI (Stratagene) was introduced into the DT40 cell maintaining an intact human chromosome 14 labeled with pSTneo [Katoh et al., *Cell Structure and Function*, 12, 575-580, 1987; Japanese Collection of Research Biologicals (JCRB) Bank, Deposit Number VE039] by electroporation (550 V, 25 μF). The electroporation method into the DT40 cell is described in the publication (Kuroiwa et al., *Nat. Biotechnol.* 18: 1086-1090, 2000).

The colony was subjected to selection by histidinol (0.5 mg/ml, Sigma) for two weeks, and thus a genomic DNA extracted from the resistant colony was subjected to PCR screening.

PCR was carried out with 40 cycles of 98° C. for 10 seconds and 68° C. for 6 minutes by using primers amplifying a clone in which the targeting occurred SC355KO-F2 (5'-acggcgtgaggaccaaggagcgaaacc-3') (SEQ ID NO:59) and SC355KO-R2 (5'-tgagcgacgaattaaaacaggcgatgac-3') (SEQ ID NO:60) and also with 40 cycles of 98° C. for 10 seconds, 60° C. for 30 seconds, and 72° C. for 1 minute by using primers amplifying a clone in which vector fragments were randomly integrated 355N-F (5'-gggcaacatagcaagacaccattc-3') (SEQ ID NO:61) and 355N-R (5'-tcctctcacctcagcctccat-agta-3') (SEQ ID NO:62).

As a result, clone 1355-2 was identified as a clone which generated the targeting.

Subsequently, in order to insert a lox511 sequence and a promoterless puro$^r$ cassette into the AL391156 region on the centromere side 85 Mb from the AL512355 site, the targeting vector p14CEN(FR)hygpuro lox511DT linearized with NotI (Roche) was introduced into 1355-2 by electroporation (550 V, 25 μF).

The colony was subjected to selection by hygromycin (1.5 mg/ml, Introgen) for two weeks, and thus a genomic DNA extracted from the resistant colony was subjected to PCR screening. It was determined by PCR under conditions of 40 cycles of 98° C. for 10 seconds and 68° C. for 5 minutes by using the primers 14CENKO-F3 (5'-actgaaatattttaaatgtttgc-catcccactcc-3') (SEQ ID NO:63) and 14CENKO-R3 (5'-agac-ctccgcgccccgcaacctccccttctac-3') (SEQ ID NO:64) ones in which the targeting occurred.

Further, a random insertion was determined by PCR under conditions of 30 cycles of 98° C. for 10 seconds, 60° C. for 30 seconds, and 72° C. for 1 minute by using the primers 14CEN (N)-F2 (5'-aacagttgaatttatggggagtc-3') (SEQ ID NO:65) and 14CEN(N)-R2 (5'-tcaggctttaaacacagtatcacag-3') (SEQ ID NO:66).

As a result, clone I156-10 was identified as a clone in which the targeting occurred.

In order to achieve a reduction from about 106 Mb to 21 Mb by deleting a sequence of about 85 Mb from the human chromosome 14 by generating a site specific recombination between two lox511 sites each disposed on the AL512355 site and the AL391156 site, a Cre expression plasmid was introduced into the I156-10 by electroporation (550 V, 25 µF).

Since the puromycin resistance was imparted by a CAG promoter-lox511-puro$^r$ cassette formed at a recombination site, the colony was cultured for 4 days and was subjected to selection by puromycin (5 µg/ml, Sigma). The sequences of PCR products were analyzed by carrying out PCR using the primers CAGpuro-F3 and CAGpuro-R3 described in Example 2(3), and thus the presence of the cassette was confirmed.

Further, in order to confirm that both of hisD and hyg$^r$ cassettes was lost as a result of deletion of the 85 Mb, the sensitivity to histidinol (0.5 mg/ml, Sigma) and hygromycin (1.5 mg/ml, Invitrogen) was analyzed. In addition, it was confirmed that the human chromosome 14 was shortened by FISH using the Human Cot-1 DNA (Invitrogen) as a probe.

In the above, clone D8 was identified as a clone in which a desired deletion was achieved.

In order to integrate a loxP sequence into a GFP code sequence on the RNR2 gene locus (Kuroiwa et al., *Nat. Biotechnol.* 27: 173-181, 2009) of the human chromosome 14, the targeting vector pRNR2loxPbsrDT linearized with SwaI (Roche) was introduced into clone D8 by electroporation (550 V, 25 µF). The colony was subjected to selection by blasticidin S (20 µg/ml, Invitrogen) for two weeks. A genomic DNA of the resistant colony was subjected to PCR screening using the primers RNR2-1 (5'-tggatgtatcctgtcaagagacc-3') (SEQ ID NO:87) and STOP-3 (5'-cagacactctatgcctgtgtgg-3') (SEQ ID NO:88) with 40 cycles of 98° C. for 10 seconds and 65° C. for 5 minutes.

As a result, clones 14D1 and 14D3 were identified as positive clones maintaining the 14D fragment.

In order to construct a chimeric IgM by substituting the CH2 domain to the TM2 domain of the human immunoglobulin µ heavy chain constant region with bovine-derived sequences, the targeting vector pCH2CAGzeoDT(F) linearized with SalI (Roche) was introduced into clone 14D1 by electroporation (550 V, 25 µF).

The colony was subjected to the Zeocin selection of 1 mg/ml for two weeks, and thus a genomic DNA of the resistant colony was subjected to PCR screening. PCR was carried out under conditions of 40 cycles of 98° C. for 10 seconds and 68° C. for 5 minutes by using the primers cHAC-F (5'-acgc-ctgctcgcctgcccgctcgcttct-3') (SEQ ID NO:67) and cHAC-R (5'-ttgccagggccacagttaacggatacg-3') (SEQ ID NO:68).

The ligated part at 5' and 3' of the bovine sequence and the human sequence was confirmed by analyzing the sequences of the PCR products by carrying out PCR under conditions of 40 cycles of 98° C. for 10 seconds, 64° C. for 30 seconds, and 72° C. for 1 minute by using the primers CH2 5'-F (5'-cagcaccccaacggcaacaaagaaa-3') (SEQ ID NO:69) and CH2 5'-R (5'-ccccagggctgcactcaccaacat-3') (SEQ ID NO:70) and of 40 cycles of 98° C. for 10 seconds and 68° C. for 8 minutes by using cHAC-F3 (5'-tgcaggtgaagtgacggccagccaagaaca-3') (SEQ ID NO:71) and cHAC-R3 (5'-tggcagcagggtgacagg-gaaggcagggaaaag-3') (SEQ ID NO:72) as primers.

Figure 15:
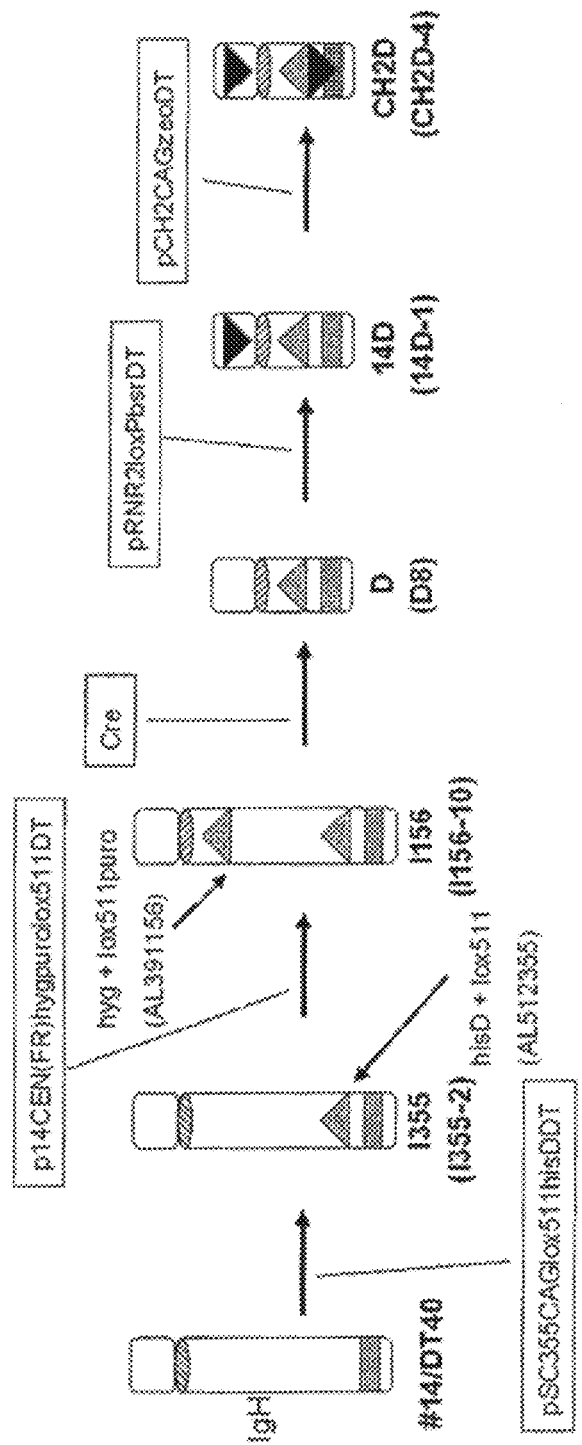
FIG. 15 illustrates an outline of a method for constructing the CH2D fragment in a DT40 cell.
Figure 16:
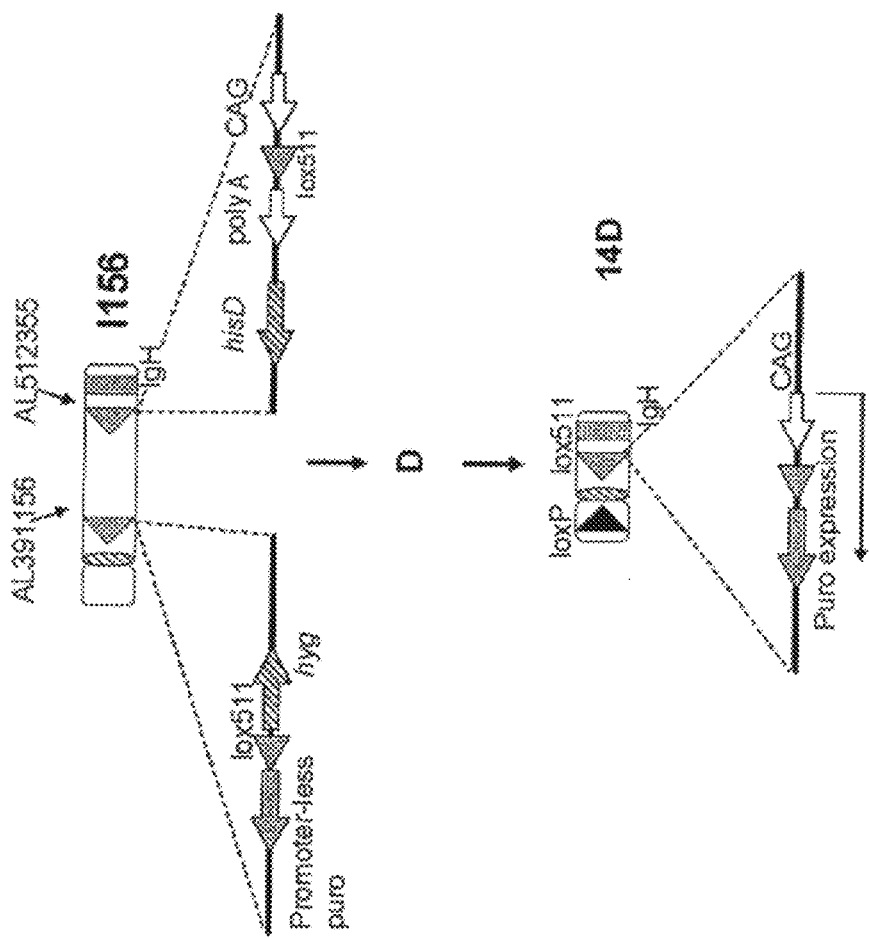
FIG. 16 illustrates an outline of a method for modifying the human chromosome 14 in a DT40 cell.

In the above, clone CH2D2-4 was identified as a positive clone which maintained the CH2D fragment. FIGS. 15 and 16 illustrate an outline of a method for modifying the human chromosome 14 in a DT 40 cell.

Example 4

Construction of cKSL-HACΔ

(1) Construction of cKSL-HACΔ in a DT40 Hybrid Cell cKSL-HACΔ was constructed in a DT40 hybrid cell according to a method described in the publication (Kuroiwa et al., *Nat. Biotechnol.* 27: 173-181, 2009).

SLKH6 comprising the hyg$^r$ cassette in Example 2(3) and CH2D-4 comprising the bs$^r$ cassette in Example 3(1) were fused by using PEG1500 (Roche) to construct a DT40 hybrid cell.

The colony was maintained in the presence of hygromycin B (1.5 mg/ml, Invitrogen) and blasticidin S (20 µg/ml, Invitrogen) for 3 weeks to select a cell maintaining both of the SLKH fragment and the CH2D fragment. A genomic DNA was extracted from the resistant colony and was subjected to PCR.

It was confirmed by PCR using the following primers whether the SLKH fragment was maintained. That is, a combination of IGKC-F and IGKC-R, a combination of IGKV-F and IGKV-R, a combination of RPIA-F and RPIA-R, a combination of EIF2AK3-F and EIF2AK3-R, a combination of cos138KO-F and cos138KO-R, a combination of CAGpuro-F3 and CAGpuro-R3, a combination of 553P-F and 553P-R, a combination of hVpreB1-F and hVpreB1-R, a combination of hVpreB3-F and hVpreB3-R, a combination of IgL-F and IgL-R, a combination of 344-F and 344-R, a combination of hL5-F and hL5-R, a combination of 350P-F and 350P-R, and a combination of 553KO-F and 553 KO (all described in Example 2) were used.

It was confirmed by PCR using the following primers whether the CH2D fragment was maintained. That is, a combination of CAGpuro-F3 and CAGpuro-R3 [described in Example 2(3)], a combination of RNR2-1 and STOP-3 [described in Example 3(1)], a combination of VH3-F (5'-agt-gagataagcagtggatg-3') (SEQ ID NO:73) and VH3-R (5'-cttgt-gctactcccatcact-3') (SEQ ID NO:74), a combination of g1(g2)-F (5'-accccaaaggccaaactctccactc-3') (SEQ ID NO:75) and g1(g2)-R (5'-cacttgtactccttgccattcagc-3') (SEQ ID NO:76), a combination of 14CENKO-F3 (5% actgaaatattt-taaatgtttgccatcccactcc-3') (SEQ ID NO:89) and 14CENKO-R3 (5'-agacctccgcgccccgcaacctcccctctac-3') (SEQ ID NO:90), a combination of CH25'-F (5'-cagcaccccaacggcaa-caaagaaa-3') (SEQ ID NO:91) and CH25'-R (5'-ccccagggct-gcactcaccaacat-3') (SEQ ID NO:92), a combination of cHAC-F3 (5'-tgcaggtgaagtgacggccagccaagaaca-3') (SEQ ID NO:93) and cHAC-R3 (5'-tggcagcagggtgacagggaaggcagg-gaaaag-3') (SEQ ID NO:94), and a combination of SC355F3R3KO-F2 (5'-gccattgtcgagcaggtagt-3') (SEQ ID NO:95) and SC355F3R3KO-R2 (5'-tccctcatcagccatcctaa-3') (SEQ ID NO:96) were used.

With regard to the PCR conditions, each PCR reaction was carried out at 40 cycles of 98° C. for 10 seconds and 68° C. for 1.5 minutes with a combination of CAGpuro-F3 and CAG-puro-R3; at 40 cycles of 98° C. for 10 seconds and 65° C. for 5 minutes with a combination of RNR2-1 and STOP-3; at 40 cycles of 98° C. for 10 seconds, 56° C. for 30 seconds, and 72° C. for 1 minute with a combination of VH3-F and VH3-R; at 40 cycles of 98° C. for 10 seconds, 60° C. for 30 seconds, and 72° C. for 1 minute with a combination of g1 (g2)-F and g1 (g2)-R; at 40 cycles of 98° C. for 10 seconds and 68° C. for 5 minutes with a combination of 14CENKO-F3 and 14CENKO-R3; at 40 cycles of 98° C. for 10 seconds, 64° C. for 30 seconds, and 72° C. for 1 minute with a combination of CH25'-F and CH25'-R; at 40 cycles of 98° C. for 10 seconds and 68° C. for 8 minutes with a combination of cHAC-F3 and cHAC-R3; at 40 cycles of 98° C. for 10 seconds, 60° C. for 30 seconds, and 72° C. for 1 minute with a combination of SC355F3R3KO-F2 and SC355F3R3KO-R2.

Further, it was confirmed by FISH using the Human Cot-1 DNA (Invitrogen) as a probe that two human chromosome fragments had an appropriate size (the SLKH fragment was about 156 Mb and the CH2D fragment was about 21 Mb).

In the above, clones cKSLD2 and cKSLD22 were identified as positive clones.

In order to induce a site specific recombination between two loxP sites arranged on the cos138 site of the SLKH fragment [Example 2(3)], respectively, and the RNR2 gene locus of the CH2D fragment [Example 3(1)] to delete the CAG promoter-zed cassette [Example 3(1)] inserted between the loxP sequences on the chimeric Igμ gene locus, a Cre expression vector was introduced into cKSLD2 and cKSLD22 by electroporation (550 V, 25 μF).

Since the GFP expression capability was imparted by the PGK promoter-loxP-GFP cassette constructed at the translocation site, recombinants were concentrated by sorting GFP positive cells using FACSAria according to a method described in the publication (Kuroiwa et al., *Nat. Biotechnol.* 18: 1086-1090, 2000).

Sorting was carried out twice to obtain a GFP positive cell group having two different GFP expression levels.

It was confirmed by PCR of 40 cycles of 98° C. for 10 seconds and 68° C. for 4 minutes by using the PCR primers PGK2 (5'-tgttctcctcttcctcatctcc-3') (SEQ ID NO:79) and GFP2 (5'-tgaaggtagtgaccagtgttgg-3') (SEQ ID NO:80) and the PCR primers CreCAGzeo-F3 (5'-gccctcaccttgcagaccac-ctccatcat-3') (SEQ ID NO:77) and CreCAGZeo-R3 (5'-cctctcctgctcagtcccctt ccttccatc3') (SEQ ID NO:78) that the CAG promoter-zed cassette on the chimeric Igμ gene locus was deleted, and thus it was suggested that a group having a low GFP expression level maintained cKSL-HACΔ which occurred a desired translocation.

Figure 17:
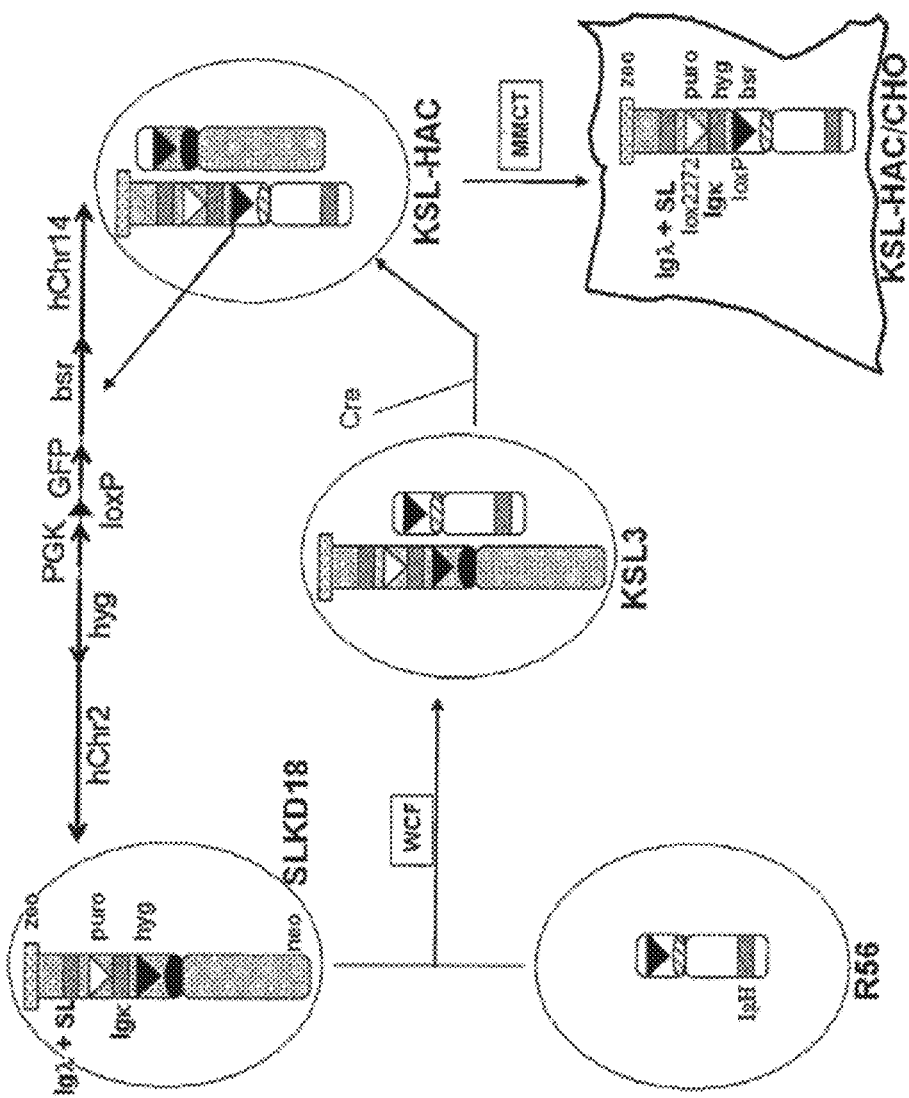
FIG. 17 illustrates an outline of a method for constructing cKSL-HACΔ in a DT40 hybrid cell.

It was confirmed that cKSLD2-derived cKSLDH2(2L) and cKSLD22-derived cKSLDH22(2L) were identified as DT40 hybrid cell lines consisting of cell groups which maintained cKSL-HACΔ and exhibited a low GFP expression level. FIG. 17 illustrates an outline of a method for constructing cKSL-HACΔ in a DT40 hybrid cell.

(2) Transfer of cKSL-HACΔ from a DT40 Hybrid Cell to a CHO Cell by MMCT method

In the following manner, cKSL-HACΔ described in Example 4(1) was transferred from the DT40 hybrid cell line cKSLDH2(2L) or cKSLDH22(2L) to the Chainese Hamster Ovary (CHO) cell by the MMCT method.

Purified micronuclei derived from cKSLDH2(2L) or cKSLDH22(2L) were fused with $2 \times 10^7$ of CHO cells by using PEG1500 (Roche), and a selection was carried out by Zeocin (800 μg/ml, Invitrogen) and Ouabain ($10^{-5}$ M, Sigma) for 3 weeks.

After Zeocin resistant colonies were harvested, a genomic DNA was extracted, and was subjected to PCR screening. It was confirmed by using the following PCR primers whether cKSL-HACΔ was maintained. That is, a combination of IGKC-F and IGKC-R, a combination of IGKV-F and IGKV-R, a combination of RPIA-F and RPIA-R, a combination of EIF2AK3-F and EIF2AK3-R, a combination of cos138KO-F and cos138KO-R, a combination of CAGpuro-F3 and CAGpuro-R3, a combination of 553P-F and 553P-R, a combination of hVpreB1-F and hVpreB1-R, a combination of hVpreB3-F and hVpreB3-R, a combination of IgL-F and IgL-R, a combination of 344-F and 344-R, a combination of hL5-F and hL5-R, a combination of 350P-F and 350P-R, and a combination of 553KO-F and 553 KO-R [all described in Example 2(3)], a combination of VH3-F and VH3-R, a combination of g1 (g2)-F and g1(g2)-R, and a combination of PGK2 and GFP2, a combination of 14CENKO-F3 and 14CENKO-R3, a combination of CH25'-F and CH25'-R, and a combination of cHAC-F3 and cHAC-R3 [all described in Example 3(1)], a combination of SC355F3R3KO-F2 and SC355F3R3KO-R2 [Example 3(2)], and a combination of CreCAGzeo-F3 and CreCAGzeo-R3 [all described in Example 4(1)] were used.

Further, it was confirmed by FISH using the Human Cot-1 DNA (Invitrogen) as a probe whether cKSL-HACΔ was maintained. In addition, the presence of the gene loci of the human immunoglobulin heavy chain (IgH), the immunoglobulin κ chain (Igκ), and the immunoglobulin λ chain (Igλ) on cKSL-HAC was confirmed by a three-color FISH using the BAC clone RP11-417P24, RP11-316G9, and RP11-22M5 from Roswell Park Cancer Institute Human Male BAC Library (RPCI-11), (Advanced Geno Techs Co.) as probes.

A Comparative Genomic Hybridization (CGH) analysis was carried out with Roche NimbleGen by the custom-made array using about 72000 probes covering the gene loci of human IgH, Igκ, and Igλ. As a result, it was revealed that clone cKSLDC6 obtained from cKSLD2(2L) by the MMCT method and clones cKSLDC15 and cKSLDC23 obtained from cKSLDH22(2L) by the MMCT method had a homologous structure.

Example 5

Construction of KcHAC
(1) Construction of KcHAC in Bovine Fibroblasts

The bovine fibroblast cell line C537 (κHAC/IGHM$^{-/-}$IG-HML1$^{-/-}$) was transfected according to a method described in the publication (Kuroiwa et al., *Nature Genetics,* 36, 775-780, 2004) except that the targeting vector pCH1CAGzeoDT was used for the Zeocin selection of 400 μg/ml.

A recombinant was identified by genome PCR at 40 cycles of 98° C. for 10 seconds and 68° C. for 8 minutes using cHAC-F3R3 (5'-tgcaggtgaagtgacggccagccaagaaca-3') (SEQ ID NO:81) and 5'-tggcagcagggtgacagggaaggcagggaaaag-3' (SEQ ID NO:82) as a primer set.

Figure 18:
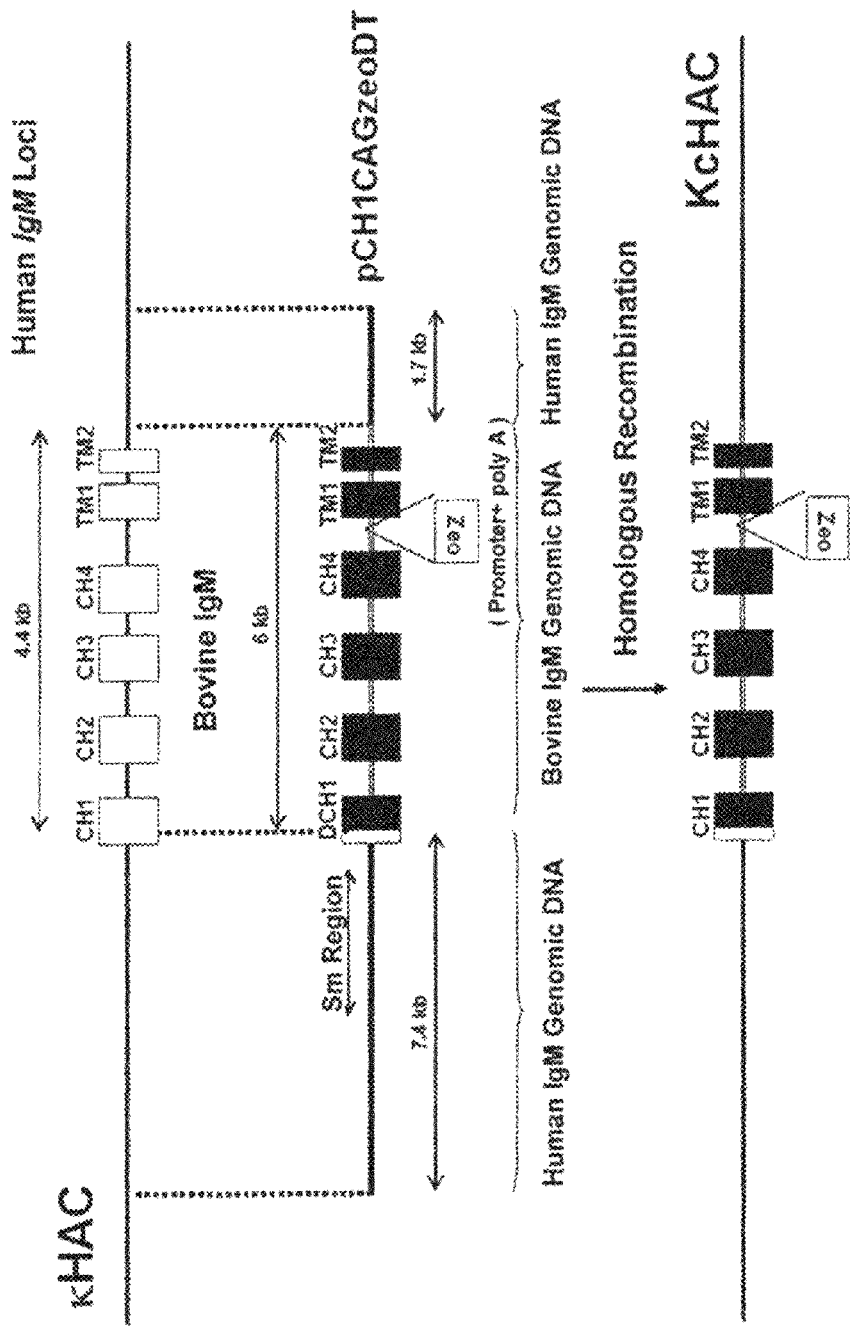
FIG. 18 illustrates an outline of a method for constructing cHAC in fibroblast cells.

Colony #30 was used for cloning to establish the 40 days gestation fetal maintaining KcHAC and the cell line C815. FIG. 18 illustrates an outline of a method for constructing cHAC in fibroblast cells.

(2) Deletion of a CAGzeo Cassette

In order to delete a CAGzeo cassette from KcHAC, the Cre expression plasmid and pBShisD/XmnI (linear) were introduced together into the cell line C815.

A colony was subjected to selection by hisD (1 mg/ml) for 2 weeks. A clone in which the CAGzeo cassette was deleted was identified by confirming that the CAGzeo cassette and the Cre sequence are not comprised by genome PCR at 40 cycles of 98° C. for 10 seconds, 65° C. or 58° C. for 30 seconds, and 72° C. for 30 seconds using zeo-F and zeo-R [consisting of nucleotide sequences of 5'-acgtcgccggagcggtc-gagttctg-3' (SEQ ID NO:83) and 5'-tcggccacgaagtgcacgcagt-tgc-3' (SEQ ID NO:84), respectively] and Cre-F and Cre-R [consisting of nucleotide sequences of 5'-aaaacaggctctagcgt-tcg-3' (SEQ ID NO:85) and 5'-ttcggatcatcagctacacc-3' (SEQ ID NO:86), respectively] as primer sets.

Colony #15 was used for cloning to produce the 40 days gestation fetal maintaining KcHAC in which CAGzeo was deleted and the cell line M112.

(3) Transfer of KcHAC from a Bovine Fibroblast to a CHO Cell by WCF Method

A cell line M112 was subjected to WCF with a CHO-K1 cell. Using PEG1500 (Roche), 2×10$^6$ of each cells were fused and drug selection was carried out in the presence of G418 (600 μg/ml, Invitrogen) and Ouabain (1×10$^{-5}$ mol/L, Sigma) for 2 to 3 weeks.

CHO-like cell colonies were subjected to screening by a set of genome PCR using a combination of CH3-F3 and CH4-R2, a combination of VH3-F3R3, a combination of IGKV-FR and IGKC-FR, and a combination of PGK2 and GFP2 as primer sets.

Clone CKF4 was identified as a donor for transferring KcHAC to a bovine fibroblast.

Example 6

Transfer of the HAC into a Bovine Cell Line for Generation of a HAC Bovine for Production of Human IgG cKSL-HACΔ was transferred from hybrid cells to CHO cells by using the MMCT method (Kuroiwa et al., *Nat. Biotechnol.* 18: 1086-1090, 2000).

The CHO clone comprising the KcHAC was cultured in F12 medium (Invitrogen) supplemented with 10% FBS (Invitrogen) and G418 (0.6 mg/ml) under conditions of 37° C. and 5% $CO_2$. In addition, the CHO clone comprising the cKSL-HACΔ was cultured in F12 medium (Invitrogen) supplemented with 10% FBS (Gibco) and Zeocin (0.8 mg/ml) under conditions of 37° C. and 5% $CO_2$.

A HAC-comprising clone was expanded in culture in 12 of T25 flasks. After the cell density reached 80 to 90%, colcemid (Sigma) was added to the medium to give a final concentration of 0.1 μg/ml.

After 3 days, the medium was exchanged with a DMEM medium (Invitrogen) supplemented with 10 μg/ml of cytochalasin B (Sigma). Micronuclei were recovered by centrifuging the flask at 8000 rpm for 60 minutes. The micronuclei were purified through 8-, 5-, and 3-μm filters (Costar), followed by resuspension in a DMEM medium. The micronuclei were used for fusion with bovine fibroblasts as described below.

Bovine fetal fibroblasts (IGHM$^{-/-}$/IGHML1$^{-/-}$, Kuroiwa et al., *Nat. Biotechnol.* 27: 173-181, 2009) were cultured in α-MEM (Invitrogen) medium supplemented with 15% FBS (Hyclone) under conditions of 38.5° C. and 6.5% $CO_2$. The fibroblasts were expanded in culture in a T175 flask. When the cell density reached 70 to 80%, the cells were separated from cells with 0.05% trypsin. The separated fibroblast cells were washed twice with a DMEM medium and then overlayed on the micronuclei suspension.

After the micronuclei-fibroblast suspension was centrifuged at 1,500 rpm for 5 minutes, PEG1500 (Roche) was added to the pellet according to the attached protocol to allow the micronuclei to be fused with the bovine fibroblasts.

Subsequently, the fused cells were plated into ten 24-well plates and cultured in an α-MEM medium supplemented with 15% FBS for 24 hours. After that, the medium was exchanged with a medium containing 0.8 mg/ml of G418 in case of KcHAC and 0.6 mg/ml of Zeocin in case of cKSL-HACΔ.

After being cultured in the presence of antibiotic materials for about two weeks, drug-resistant fused cells were selected.

The selected fused cells comprising various HACs were used as a chromatin donor, and thus a bovine comprising various HACs was produced by a chromatin transfer method described in WO2002/051997.

Example 7

Evaluation of the Human IgG Level in HAC Bovine Serum

The human IgG levels in various HAC bovine sera constructed were measured by a method described in the publication (Kuroiwa et al., *Nat. Biotechnol.* 27: 173-181, 2009). The total amount of the human IgG in each serum of 6-month-old HAC bovines is shown in the following FIG. 19. Further, the average value of the total amount of the human IgG in various 6-month-old HAC bovine sera is shown in the following Table 3.

TABLE 3

| Total Amount of the Human IgG in Bovine Serum of Various 6-Month-Old HAC Bovines (μg/mL) | | |
|---|---|---|
| κHAC | KcHAC | cKSL-HACΔ |
| 433.9 | 1252 | 4172 |

Figure 19:
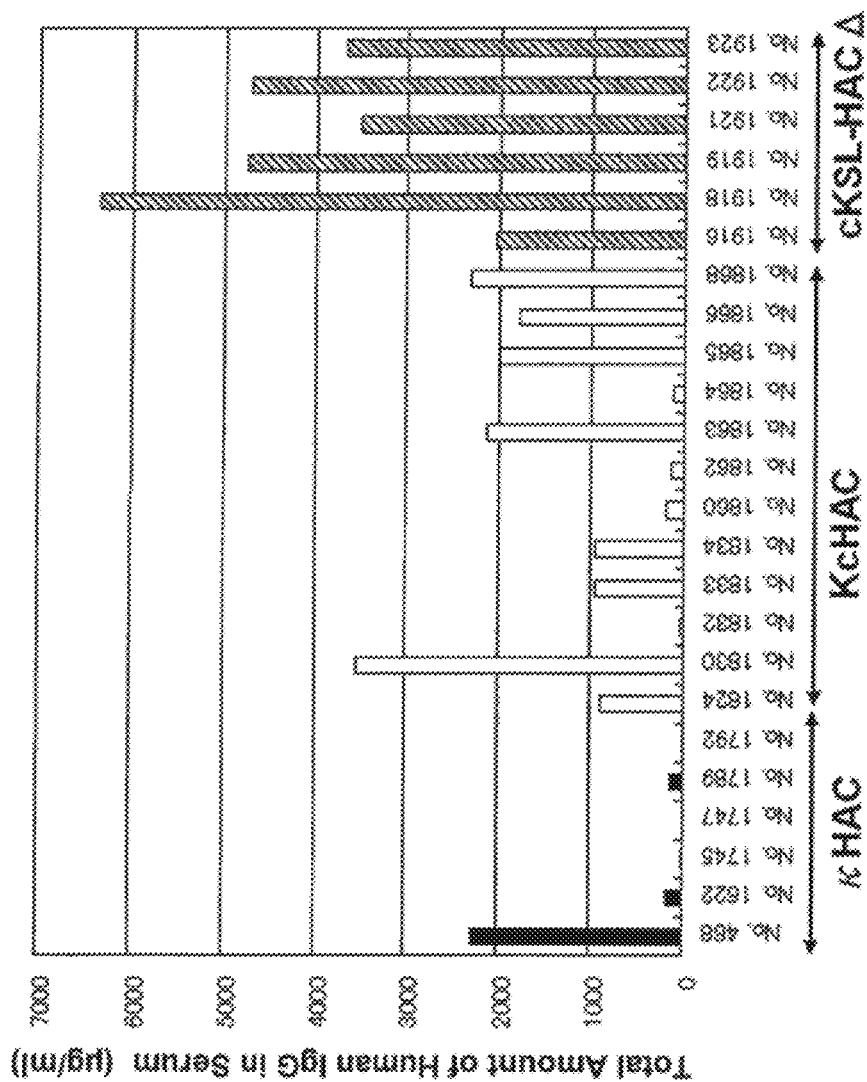
FIG. 19 illustrates a total amount of the human IgG in each serum of 6-month-old HAC bovines.

As shown in FIG. 19 and Table 3, the amount of human IgG production in serum in bovines having KcHAC or cKSL-HACΔ was significantly increased as compared to bovines having κHAC.

In addition, according to the publication (Kuroiwa et al., *Nat. Biotechnol.* 27: 173-181, 2009), the B cell profile in HAC bovine peripheral blood and lymph node was analyzed by flow cytometry. As a result, the number of B cells expressing IgM in the KcHAC bovine and cKSL-HACΔ bovine peripheral blood was increased as compared to that in the κHAC bovine peripheral blood. Further, the number of B cells expressing IgM even in the KSL-HAC bovine and the cKSL-HACΔ bovine lymph nodes was increased as compared to the number in the κHAC bovine lymph node.

Example 8

Production of the Human IgG to the Anthrax Protective Antigen by the HAC
Bovines In order to evaluate that HAC bovines could initiate antigen specific humoral responses against a known single antigen due to human IgG, anthrax protective antigens (hereinafter referred to as PA) were used and reviewed. According to a description in the publication (Kuroiwa et al., *Nat. Biotechnol.* 27: 173-181, 2009), three KcHAC/IGHM$^{-/-}$ IGHML1$^{-/-}$ bovines (No. 1710, No. 1824, and No. 1834) were immunized with PA and was measured the titer of PA specific human IgG. The results are shown in Table 4.

TABLE 4

| Production amount of the PA specific human IgG in the KcHAC bovine (U/mg IgG) | | | | |
|---|---|---|---|---|
| | Second Immunization | Third Immunization | Fourth Immunization | Fifth Immunization |
| No. 1710 | 62607 | | | |
| No. 1824 | 26481 | | | |
| No. 1834 | 11972 | 31007 | 39342 | 39745 |

As a result, KcHAC bovines produced PA specific human IgG of about 12000 to 63000 U/mg IgG at a time point of the second immunization, and in No. 1834, whenever the immunization was repeated to the fifth immunization, the titer production amount of the PA specific human IgG was increased.

Example 9

Production of Human IgG Specific to T Cell Surface Membrane Protein Mixture by HAC Bovines In order to evaluate that HAC bovines could initiate antigen specific humoral responses against an unknown complex antigen due to human IgG, a T cell surface membrane protein mixture (fraction of CEM cell membrane formulation, hereinafter referred to as CEM) was used as an antigen and examined.

(1) Culture of CEM Cell

By using A RPMI1640 medium (ATCC) comprising 10% bovine fetal serum (Hyclone), the human T cell line CCRF-CEM (ATCC) was allowed to proliferate in a constant humidity and temperature chamber at 37° C. and 5% $CO_2$ until the cells in a flask of 225 $cm^2$ was confluent ($2\times10^6$ cells/mL).

Into a 850 $cm^2$ roller bottle (Corning) with a bent cap, 500 mL of the RPMI1640 medium containing 10% bovine fetal serum was dispensed and the cells were seeded at a density of $2\times10^5$ cells/mL.

The roller bottle was put on a roller bottle culturing apparatus (Thermo Scientific) and the cells were cultured for 5 days. In order to recover the CEM cells from the roller bottle, the culture was poured into a 2 L sterilized polypropylene biobottle (Nalgen).

Subsequently, the cells were made into a pellet by centrifugation using a Sorvall RC12BP at 450×g and 2 to 8° C. for 30 minutes. The cell pellet was resuspended into sterilized iced PBS, followed by washing operation twice.

After the final washing, the cell pellet was suspended at a density of $2\times10^8$ cells/mL in an iced lysis buffer (20 mM Tris chloride, 10 mM NaCl, and 0.1 mM $MgCl_2$) comprising 1 mM PMSF (Sigma), various protease inhibitors [1.6 µM Aprotinin, 40 µM Leupeptin, 2 mM AEBSF, 0.1 mM Bestatin, 30 µM E-64, and 20 µM PepstatinA (CalBioChem)], and 25.6 µg/ml DNAseI (Sigma). Then, the cells were immediately frozen in liquid nitrogen. The frozen cells were stored at −80° C. until further use.

(2) Isolation of CEM Cell Membrane by Sucrose Density-Gradient Centrifugation

The frozen CEM cells were melted in a cooling water bath. In order to break up the cell membranes, the CEM cells were subjected to ultrasonication twice to three times in a cooling water bath under conditions of 40 amps and 30 seconds by using an ultra sonic processor (Sonics & Materials).

After the crushed material was injected into the bottom of the lysis buffer in the sterilized ultra clear centrifuge tube with a pipette by using a cooled 41% (w/v) sucrose solution, centrifugation was carried out using an ultracentrifuge of Beckman at 83,000×g (SW 32 Ti rotor) for 1 hour at 4° C.

A cloud-like intermediate layer comprising the CEM cell membrane which was formed between the sucrose layer and the lysis buffer layer was recovered and transferred to a polycarbonate ultracentrifuge tube, followed by dilution using a sterilized iced PBS to have a ratio of 1:3.

The CEM membranes were made into a pellet by ultracentrifugation at 80,000×g (70.1 Ti rotor) for 50 minutes at 4° C. After supernatant was carefully removed with a sterilized Pasteur pipette, the CEM membranes were once washed by ultracentrifugation at 4° C. for 50 minutes by using sterilized iced PBS.

Finally, the CEM cell membranes were resuspended in PBS. In order to crush the membrane pellet, the CEM cell membranes were subjected to ultrasonication in a cooling water bath under conditions of 20 amps and 30 seconds by using an ultrasonic processor. The CEM membrane crushed material was stored at −80° C. until further use.

(3) Preimmunization of CEM Membrane

Against four KcHAC/IGHM$^{-/-}$IGHML1$^{-/-}$ bovine (No. 1863, No. 1865, No. 1868, No. 1735) and two cKSL-HACΔ/IGHM$^{-/-}$IGHML1$^{-/-}$ bovine (No. 1922, No. 1923), immunization was carried out with a CEM membrane preparation at 3 mg/run.

The CEM membrane preparation was prepared by Montanide ISA 25 adjuvant (Seppic) which was an oil-in-water type emulsion with a saponin-derived immune inducer QuilA (Accurate Chemicals). Bovine was immunized four times at intervals of 4 weeks. The vaccine was intramuscularly inoculated to the cervical region (2 mL/dose).

For measurement of antibody titer, serum samples were collected prior to immunization and on days 10 and 14 after immunization. After blood was allowed to stand still in a serum separation tube to clot, and serum was separated by centrifugation. Further, the serum was dispensed at 0.5 to 1 mL, and freezed and stored until future assay. The titer of anti-CEM antibody was determined by CEM cell specific human IgG ELISA.

(4) CEM Cell Specific ELISA Assay

Four dilution series were prepared by using a 5% membrane Block/PBS (GE Healthcare) buffer from a serum sample.

In order to prepare a standard curve, seven-step concentration series which was diluted by 2.5 times from 275 times to 67,139 times were prepared by using a serum with a high titer obtained from a CEM immune animal of which a final titer determined in advance as an authentic preparation and using 5% Membrane Block/PBS.

The inverse number of the final concentration was employed as a unit of titer and a final titer determined in the case of an authentic preparation was defined as 55,000 units. With regard to positive control serum and negative control serum, dilution series were prepared with 5% Membrane Block/PBS and used as an internal standard for confirming the consistency of the assay.

In order to determine the titer of the CEM specific human IgG, 50 µL of samples (authentic preparation serum dilution for correction, positive control serum dilution, negative control serum dilution, and measurement sample serum dilution) were injected in duplicate into a U-shaped bottom 96 well-microplate (Costar), and 50 µL of the CEM cells ($4\times10^6$ cells/mL) was added thereto.

After the plate was allowed to stand still at 4° C. for 60 minutes, the plate was washed with 100 to 200 µL of PBS three times to remove non-bound proteins. After each washing operation, the plates were subjected to centrifugation at 2850×g for 5 minutes to carefully suck in and remove supernatant from each well.

After three washing operations, 100 µL of HRP-labeled donkey anti-human IgG antibody (Jackson Immuno Research) diluted with 5% Membrane Block/PBS buffer by 50,000 times was added to each well to resuspend the cell pellet in a HRP solution. After the plate was allowed to stand still at 4° C. for 30 minutes, the plate was washed with PBS three times same as above.

Finally, the bound anti-CEM antibody was detected by dividing 100 µL/well of the TMB+$H_2O_2$ matrix mixture solution (KPL) into the plate, and the plate was also allowed to stand still at 25° C. for 15 minutes. After the chromogenic reaction was stopped by 100 μL/well of 10% phosphoric acid, 450 nm was measured by using a microplate reader (Biotek Instruments).

A four-parameter standard curve was prepared from values of seven-step dilution series, and a value of the serum sample was calculated by intrapolation on the curve with Gen5Secure Software. An average titer was calculated by carrying out a dilution assay three to four times for each measurement serum sample.

Figure 20:
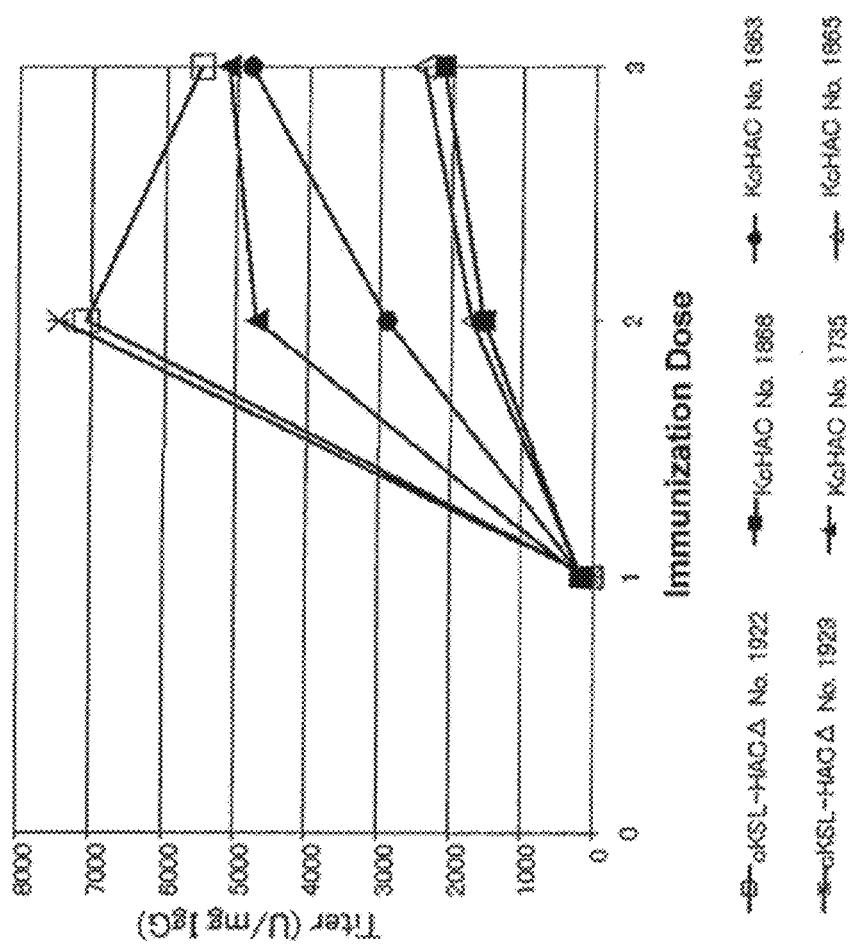
FIG. 20 illustrates the result of a CEM cell specific ELISA assay.

The result is shown in FIG. 20. Further, the titer of the CEM specific human IgG in each HAC bovine sera after the second CEM administration is shown in Table 5. After the second CEM administration, it was shown that the CEM specific human IgG was produced at about 7000 U/mg IgG in the cKSL-HACΔ bovine, and at about 1700 to 4700 U/mg IgG in the KcHAC bovine among the total human IgG.

Production of the CEM Specific Human IgG (U/mg IgG)

| Kinds of HAC | Bovine No. | CEM specific human IgG |
| --- | --- | --- |
| cKSL-HACΔ | No. 1922 | 7056.461 |
|  | No. 1923 | 7449.184 |
| KcHAC | No. 1863 | 2880.773 |
|  | No. 1865 | 1691.688 |
|  | No. 1868 | 1528.455 |
|  | No. 1735 | 4697.248 |

REFERENCE EXAMPLE

Reference Example 1

Establishment of Mouse A9 Cell Maintaining Human Chromosome 2, 14, and 22

According to a method described in WO1998/037757, a plasmid pSTneo [Katoh et al., *Cell Structure and Function*, 12, 575-580, 1987; Japanese Collection of Research Biologicals (JCRB) Bank, Deposit No. VE039] is introduced into a human normal fibroblast HFL-1 (RIKEN Japan Cell Bank, Deposit No. RCB0251) to obtain a transformed cell.

After that, cell fusion of the transformed cell with a mouse fibroblast A9 (Oshimura et al., *Environmental Health Perspectives*, 93, 57-58, 1991; JCRB Cell Bank, Deposit No. JCRB0211) is carried out to construct a hybrid cell.

Subsequently, according to a method described in WO1998/037757, micronuclei are prepared from the hybrid cell to be fused with the mouse A9 cell. Each clone comprising desired human chromosome 2, 14, and 22 is identified from obtained clones by genome PCR, genomic Southern Analysis, fluorescence in situ hybridization (FISH), and the like.

Reference Example 2

Construction of the DT40 Hybrid Cell kTL1 Containing a Human Chromosome 2 Fragment By a micronucleus fusion method described in WO2008/013067, the human chromosome 2 is introduced from the A9 cell comprising the human chromosome 2 obtained in Reference Example 1 into the chicken B cell DT40 (JCRB Cell Bank, Deposit No. JCRB2221).

Subsequently, a telomere sequence is inserted into the CD8A gene locus on the human chromosome 2 by introducing a targeting vector pTELPuroCD8A (Kuroiwa et al., *Nature Biotechnology*, 18, 1086-1090, 2000) into the DT40 hybrid cell by using a telomere truncation method described in WO2008/013067, and the truncation of the chromosome is induced at the insertion site.

A DT40 hybrid cell kTL1 comprising a human chromosome 2 which has a deleted region from the CD8A gene locus to the telomere end may be constructed by the manipulation.

Reference Example 3

Construction of the DT40 Hybrid Cell 52-18 Containing the Human Chromosome

By a micronucleus fusion method described in WO2008/013067, the human chromosome 22 is introduced from the A9 cell comprising the human chromosome 22 obtained in Reference Example 1 into the chicken B cell DT40 (JCRB Cell Bank, Deposit No. JCRB2221). A DT40 hybrid cell 52-18 comprising the human chromosome 22 may be constructed by the manipulation.

Reference Example 4

Construction of the DT40 Hybrid Cell R56Containing a Human Chromosome 14 Fragment According to a description of a report by Kuroiwa et al. (Kuroiwa et al., *Nature Biotechnology*, 18, 1086-1090, 2000), a loxP sequence is inserted into the RNR2 gene locus on the human chromosome 14 by introducing a targeting vector pRNR2loxPbsr (Kuroiwa et al., *Nature Biotechnology*, 18, 1086-1090, 2000) into a DT40 cell (International Patent Organism Depositary, National Institute of Advanced Industrial Science and Technology (AIST), Deposit No. FERMBP-7583) comprising the human chromosome 14 fragment SC20. The DT40 hybrid cell R56 comprising SC20 which has the loxP sequence at the RNR2 gene locus may be constructed by the manipulation.

Reference Example 5

Construction of the DT40 Hybrid Cell #14/DT40 Containing the Human Chromosome 14

By a micronucleus fusion method described in WO2008/013067, the human chromosome 14 is introduced from the A9 cell comprising the human chromosome 14 obtained in Reference Example 1 into the chicken B cell DT40 (JCRB Cell Bank, Deposit No. JCRB2221). The DT40 hybrid cell #14/DT40 comprising the human chromosome 14 may be constructed by the manipulation.

While the present invention has been described in detail and with reference to specific embodiments thereof, it will be apparent to one skilled in the art that various changes and modifications can be made therein without departing from the spirit and scope of the present invention. In this connection, this application is based on a U.S. provisional application filed on Nov. 17, 2009 (U.S. provisional application No. 61/261,935), the entire contents thereof being thereby incorporated by reference.

INDUSTRIAL APPLICABILITY

The present invention provides a human artificial chromosome vector comprising a gene encoding the human antibody heavy chain, a gene encoding the human antibody light chain, and a gene encoding IgM heavy chain constant region derived from a non-human animal; and being capable of producing a human antibody with a higher efficiency when the vector is introduced into an animal. By immunizing the animal produced using a human artificial chromosome vector of the present invention with a desired antigen, a large quantity of human polyclonal antibodies can be supplied.

The invention claimed is:

1. A human artificial chromosome (HAC) vector, wherein the HAC comprises:
   a) a gene encoding a human antibody heavy chain, wherein the gene encoding the human antibody heavy chain encodes at least a human IgG (γ) heavy chain, a human IgA (α) heavy chain or both human IgG and IgA heavy chains,
   b) a gene encoding a human antibody light chain, and
   c) a gene encoding a chimeric IgM (μ) heavy chain constant region, wherein the gene encoding the chimeric IgM heavy chain constant region comprises a human IgM heavy chain constant region gene substituted with DNA encoding an ungulate IgM heavy chain constant region gene; wherein the gene encoding the chimeric IgM heavy chain constant region encodes constant region (CH) domains CH1, CH2, CH3 and CH4, and transmembrane domains (TM) TM1 and TM2; and wherein the encoded human CH4, TM1 and TM2 domains are completely substituted with the encoded CH4, TM1 and TM2 domains of the ungulate IgM heavy chain constant region gene.

2. The HAC vector of claim 1, wherein the encoded human CH3 domain is completely substituted with the encoded CH3 domain of an ungulate IgM heavy chain constant region.

3. The HAC vector of claim 2, wherein the encoded CH2 domain is a chimeric ungulate-human CH2 domain.

4. The HAC vector of claim 2 wherein the encoded human CH2 domain is completely substituted with the encoded CH2 domain of an ungulate IgM heavy chain constant region gene.

5. The HAC vector of claim 4, wherein the encoded CH1 domain is a chimeric ungulate-human CH1 domain.

6. The HAC vector of claim 4, wherein the encoded human CH1 domain is completely substituted with the encoded CH1 domain of an ungulate IgM heavy chain constant region gene.

7. The HAC vector of claim 1, wherein the gene encoding the human antibody heavy chain in part a) encodes human IgA (α), human IgD (δ), human IgE (ε), human IgG (γ) and human IgM (μ) heavy chains.

8. The HAC vector of claim 1, wherein the gene encoding the human antibody heavy chain in part a) comprises a human chromosome 14 fragment comprising the 14q32 region.

9. The HAC vector of claim 1, wherein the gene encoding a human antibody light chain in part b) encodes either kappa (κ) human antibody light chain or lambda (λ) human antibody light chain, or both κ and λ human antibody light chains.

10. The HAC vector of claim 1, wherein the HAC vector further comprises a gene encoding a human antibody surrogate light chain selected from the group consisting of VpreB1, VpreB3, and λ5.

11. The HAC vector of claim 1, wherein the ungulate genes are bovine genes.

12. The HAC vector of claim 2, wherein the ungulate genes are bovine genes.

13. The HAC vector of claim 3, wherein the ungulate genes are bovine genes.

14. The HAC vector of claim 4, wherein the ungulate genes are bovine genes.

15. The HAC vector of claim 5, wherein the ungulate genes are bovine genes.

16. The HAC vector of claim 6, wherein the ungulate genes are bovine genes.

17. An ungulate having the HAC vector of claim 1.

18. The ungulate of claim 17, wherein the ungulate is a bovine.

19. A method for producing a human antibody, comprising:
　a) administering a target antigen into a transgenic ungulate having the HAC vector of claim 1;
　b) accumulating the human antibody specific to the antigen in serum of the transgenic ungulate, and
　c) recovering the human antibody specific to the antigen from the serum;
　wherein the ungulate produces a serum concentration of at least 1,000 ug/mL of human IgG.

20. The method of claim 19, wherein the ungulate immunoglobulin M (μ) heavy-chains are inactivated (IGHM$^{-/-}$ and IGHML1$^-$).

21. The method of claim 19, wherein the ungulate is a bovine.

22. A method for producing a human antibody, comprising:
　a) administering a target antigen into a transgenic bovine having the HAC vector of claim 1;
　b) accumulating the human antibody specific to the antigen in serum of the transgenic bovine, and
　c) recovering the human antibody specific to the antigen from the serum.

* * * * *